US010542934B2

(12) United States Patent
Bogdanovich et al.

(10) Patent No.: US 10,542,934 B2
(45) Date of Patent: *Jan. 28, 2020

(54) GARMENT SYSTEM PROVIDING BIOMETRIC MONITORING

(71) Applicant: CIPHER SKIN, Wheat Ridge, CO (US)

(72) Inventors: Phillip Bogdanovich, Evergreen, CO (US); Craig Weller, Evergreen, CO (US)

(73) Assignee: Cipher Skin, Wheat Ridge, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/049,114

(22) Filed: Jul. 30, 2018

(65) Prior Publication Data

US 2019/0046114 A1 Feb. 14, 2019

Related U.S. Application Data

(63) Continuation-in-part of application No. 15/906,046, filed on Feb. 27, 2018, which is a continuation of (Continued)

(51) Int. Cl.
*A61B 5/00* (2006.01)
*A61B 5/11* (2006.01)

(Continued)

(52) U.S. Cl.
CPC .......... *A61B 5/6804* (2013.01); *A61B 5/0002* (2013.01); *A61B 5/0205* (2013.01);

(Continued)

(58) Field of Classification Search
CPC ... A61B 5/6804; A61B 5/0002; A61B 5/0205; A61B 5/0806; A61B 5/1116;

(Continued)

(56) References Cited

U.S. PATENT DOCUMENTS 8,475,371 B2 7/2013 Derchak et al.
9,131,892 B2 * 9/2015 Markel ................ A61B 5/0015

(Continued)

FOREIGN PATENT DOCUMENTS

WO 2017065272 A1 4/2017
WO 2018116424 A1 6/2018
WO 2018123034 A1 7/2018

OTHER PUBLICATIONS

Non-final Office Action, U.S. Appl. No. 14/931,545 dated Feb. 11, 2016, 22 pages.

(Continued)

*Primary Examiner* — Emily C Terrell
(74) *Attorney, Agent, or Firm* — Akerman LLP; Mammen (Roy) P. Zachariah, Jr.

(57) ABSTRACT

A garment (e.g., a shirt) for monitoring biometric properties of the wearer of the garment is disclosed. The garment may include sensors for monitoring or assessing biometric properties such as, but not limited to, respiration properties, heart properties, and motion properties. These properties may be assessed together to provide an assessment of vital signs and body position (e.g., three-dimensional body position) of the wearer of the garment.

22 Claims, 19 Drawing Sheets

Related U.S. Application Data application No. 15/431,495, filed on Feb. 13, 2017, now Pat. No. 9,918,674, which is a continuation of application No. 14/931,545, filed on Nov. 3, 2015, now Pat. No. 9,556,033.

(60) Provisional application No. 62/074,521, filed on Nov. 3, 2014.

(51) Int. Cl.
*A61B 5/0205* (2006.01)
*A61B 5/08* (2006.01)

(52) U.S. Cl.
CPC .......... *A61B 5/1116* (2013.01); *A61B 5/0816* (2013.01); *A61B 5/1112* (2013.01)

(58) Field of Classification Search
CPC . A61B 5/6805; A61B 5/02455; A61B 5/0816; A61B 5/1112; A61B 5/1128; G16B 99/00
USPC ................ 340/870.07, 539.11–539.13, 539.1
See application file for complete search history.

(56) References Cited

U.S. PATENT DOCUMENTS

| | | | |
|---|---|---|---|
| 9,566,033 B2 | 2/2017 | Bogdanovich et al. | |
| 9,918,674 B2 | 3/2018 | Bogdanovich et al. | |
| 10,065,074 B1 | 9/2018 | Hoang et al. | |
| 2005/0054941 A1 | 3/2005 | Ting et al. | |
| 2007/0050715 A1* | 3/2007 | Behar | A61B 5/0002 715/706 |
| 2009/0012408 A1 | 1/2009 | Nagata et al. | |
| 2009/0287191 A1* | 11/2009 | Ferren | A61B 5/0031 604/891.1 |
| 2009/0326981 A1* | 12/2009 | Karkanias | G06Q 10/10 705/3 |
| 2010/0026479 A1 | 2/2010 | Tran | |
| 2012/0139731 A1 | 6/2012 | Razoumov et al. | |
| 2012/0188083 A1 | 7/2012 | Miller, II | |
| 2012/0246795 A1 | 10/2012 | Scheffler et al. | |
| 2013/0192071 A1 | 8/2013 | Esposito et al. | |
| 2013/0337974 A1* | 12/2013 | Yanev | G06F 19/3481 482/8 |
| 2013/0338472 A1 | 12/2013 | Barber et al. | |
| 2014/0070957 A1 | 3/2014 | Longinotti-Buitoni et al. | |
| 2015/0335288 A1 | 11/2015 | Toth et al. | |
| 2015/0366504 A1* | 12/2015 | Connor | A61B 5/6804 600/301 |
| 2016/0187166 A1 | 6/2016 | Ranky et al. | |
| 2018/0242912 A1 | 8/2018 | Amimori et al. | |
| 2018/0332702 A1 | 11/2018 | Nakajima et al. | |

OTHER PUBLICATIONS

Notice of Allowance, U.S. Appl. No. 14/931,545 dated Sep. 30, 2016, 13 pages.
Notice of Allowance, U.S. Appl. No. 15/431,495 dated Nov. 14, 2017, 13 pages.
Non-final Office Action, U.S. Appl. No. 15/906,046 dated Sep. 26, 2018, 20 pages.
Final Office Action, U.S. Appl. No. 15/906,046 dated Mar. 22, 2019, 22 pages.

* cited by examiner

GARMENT SYSTEM PROVIDING BIOMETRIC MONITORING

PRIORITY CLAIM

This application is a continuation-in-part of U.S. patent application Ser. No. 15/906,046, filed on Feb. 27, 2018, which is a continuation of U.S. patent application Ser. No. 15/431,495 (now U.S. Pat. No. 9,918,674 issued on Mar. 20, 2018), filed on Feb. 13, 2017, which is a continuation of U.S. patent application Ser. No. 14/931,545 (now U.S. Pat. No. 9,566,033 issued on Feb. 14, 2017), filed on Nov. 3, 2015, which claims priority to U.S. Provisional Patent Application No. 62/074,521, filed on Nov. 3, 2014, all of which are hereby incorporated by reference in their entirety.

BACKGROUND OF THE INVENTION

1. Field of the Invention

Embodiments disclosed herein relate to a garment system. Certain embodiments disclosed herein relate to a garment system for monitoring biometric information including vital signs and body motion.

2. Description of the Relevant Art

Wearable technology has become an increasingly more common resource for users to track and monitor their biometric data during physical activity and/or day-to-day activity. Devices such as wristbands, glasses, and watches may function to gather biometric data from an individual's body such as heart rate, force on a body, acceleration of a body, etc. These devices, however, may not be capable of tracking or generating a complex profile of a user's biometric data in combination with movement and body position of the user. Thus, there is still a need for a system (e.g., a garment system) that is capable of generating such data for real-time analysis of an individual's condition.

SUMMARY

In certain embodiments, a system includes a fabric for being worn on a body of a wearer. The fabric may include comprises one or more layers with at least one layer of fabric including a conductive elastic material. A plurality of respiratory monitoring sensors may be integrated in the fabric. At least two respiratory monitoring sensors may be coupled with at least a portion of the conductive elastic material. The at least two respiratory monitoring sensors may be configured to assess a resistance of the portion of the conductive elastic material between the at least two respiratory monitoring sensors. One or more inertial measurement units may be integrated in the fabric. The inertial measurement units may be configured to assess a physical position of the body of the wearer in a three-dimensional space. One or more heart rate monitors may be integrated in the fabric. The heart rate monitors may be configured to assess one or more properties associated with a heart of the wearer. A processor may be integrated in the fabric. The processor may be configured to receive data from the respiratory monitoring sensors, the inertial measurement units, and the heart rate monitors. The processor may be configured to assess one or more vital signs and a body position of the wearer of the fabric using the received data.

In certain embodiments, a method includes receiving, in a processor integrated in a fabric, data from a plurality of respiratory monitoring sensors integrated in the fabric. At least two respiratory monitoring sensors may be coupled with at least a portion of a conductive elastic material. The data from the respiratory monitoring sensors may include a resistance of the portion of the conductive elastic material between the at least two respiratory monitoring sensors. The fabric may include one or more layers with at least one layer of fabric including the conductive elastic material. Data from one or more inertial measurement units integrated in the fabric may be received in the processor. The data from the inertial measurement units may include a physical position of the body of the wearer in a three-dimensional space. Data from one or more heart rate monitors integrated in the fabric may be received in the processor. The data from the heart rate monitors may include one or more properties associated with a heart of the wearer. The processor may assess one or more vital signs and a body position of the wearer of the fabric using the data received from the respiratory monitoring sensors, the data received from the inertial measurement units, and the data received from the heart rate monitors.

BRIEF DESCRIPTION OF THE DRAWINGS

Features and advantages of the methods and apparatus described herein will be more fully appreciated by reference to the following detailed description of presently preferred but nonetheless illustrative embodiments when taken in conjunction with the accompanying drawings in which.

Figure 1:
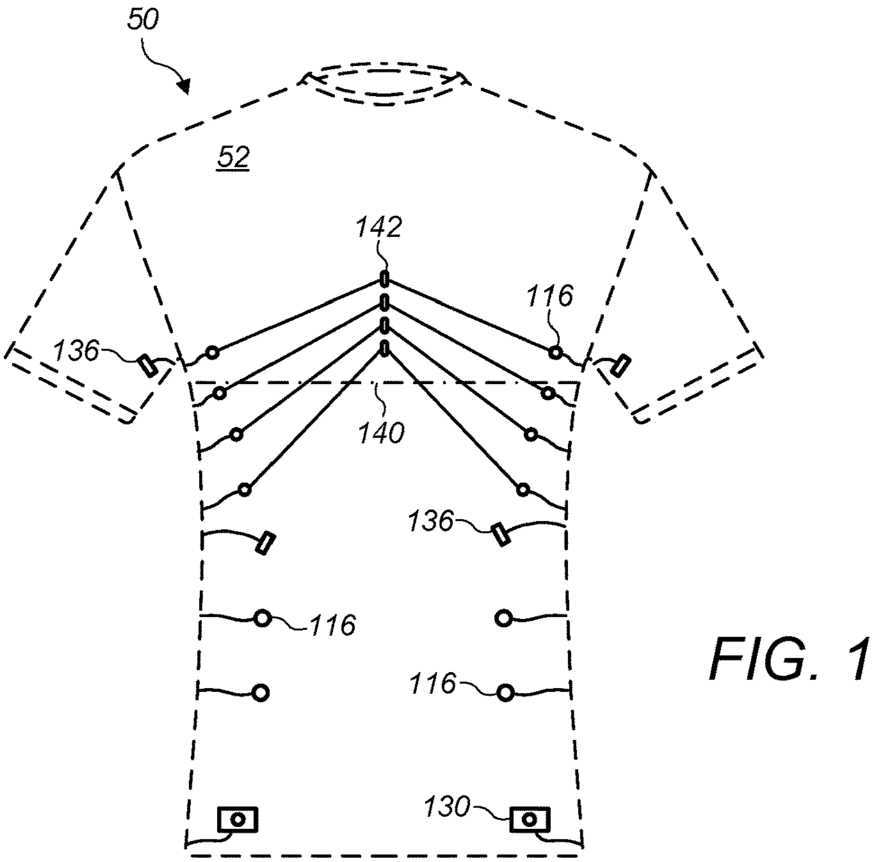
FIG. 1 depicts an anterior view representation of an embodiment of a garment system.

While the disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form illustrated, but on the contrary, the intention is to cover all modifications, equivalents and alternatives falling within the spirit and scope of the present disclosure as defined by the appended claims. The headings used herein are for organizational purposes only and are not meant to be used to limit the scope of the description. As used throughout this application, the word “may” is used in a permissive sense (i.e., meaning having the potential to), rather than the mandatory sense (i.e., meaning must). Similarly, the words “include,” “including,” and “includes” mean including, but not limited to. Additionally, as used in this specification and the appended claims, the singular forms “a”, “an”, and “the” include singular and plural referents unless the content clearly dictates otherwise. Furthermore, the word “may” is used throughout this application in a permissive sense (i.e., having the potential to, being able to), not in a mandatory sense (i.e., must). The term “include,” and derivations thereof, mean “including, but not limited to.” The term “coupled” means directly or indirectly connected.

Various units, circuits, or other components may be described as “configured to” perform a task or tasks. In such contexts, “configured to” is a broad recitation of structure generally meaning “having structure that” performs the task or tasks during operation. As such, the unit/circuit/component can be configured to perform the task even when the unit/circuit/component is not currently on. Similarly, various units/circuits/components may be described as performing a task or tasks, for convenience in the description. Such descriptions should be interpreted as including the phrase “configured to.” Reciting a unit/circuit/component that is configured to perform one or more tasks is expressly intended not to invoke 35 U.S.C. § 112(f) interpretation for that unit/circuit/component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

DETAILED DESCRIPTION OF EMBODIMENTS

The following examples are included to demonstrate preferred embodiments. It should be appreciated by those of skill in the art that the techniques disclosed in the examples which follow represent techniques discovered by the inventor to function well in the practice of the disclosed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosed embodiments.

This specification includes references to “one embodiment” or “an embodiment.” The appearances of the phrases “in one embodiment” or “in an embodiment” do not necessarily refer to the same embodiment, although embodiments that include any combination of the features are generally contemplated, unless expressly disclaimed herein. Particular features, structures, or characteristics may be combined in any suitable manner consistent with this disclosure.

Figure 2:
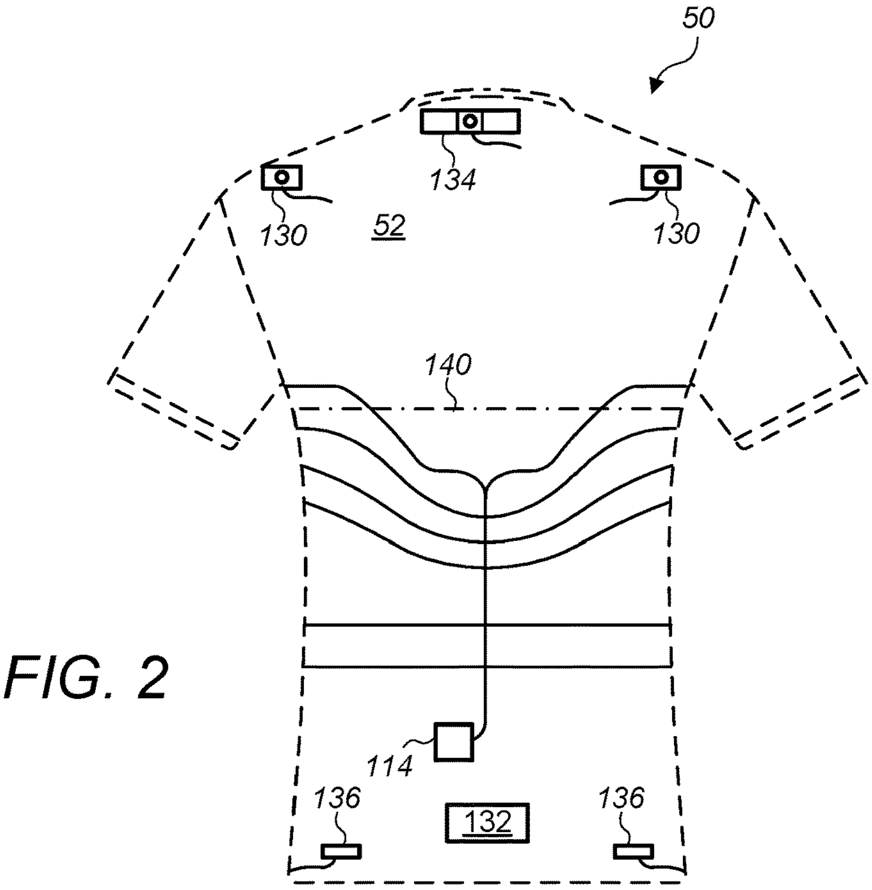
FIG. 2 depicts a posterior view representation of the embodiment of a garment system.

FIG. 1 depicts an anterior view representation of an embodiment of garment system 50. FIG. 2 depicts a posterior view representation of the embodiment of garment system 50. In certain embodiments, garment system 50 includes body 52. Body 52 may be, for example, a shirt body or any other garment wearable by a user (e.g., a person or an animal) such as an arm sleeve, a leg sleeve, or a torso sleeve. In certain embodiments, garment body 52 is constructed of a quick dry material with antistatic and anti-microbial properties. In some embodiments, garment body 52 is form fitting (athletic fit) around a portion of the user’s (wearer’s body). For example, garment body 52 may include one or more fabric layers with elastic fibers similar to spandex. Garment body 52 may include a plurality of fabrics or yarns arranged in a woven and/or a knit pattern.

Garment body 52 may house a number of electronic components either within or on the garment structure. In some embodiments, garment body 52 is made of a quick dry elastic polymer blend that provides support to the garment body wearer. Garment body 52 may include welded non-chafing seams and/or other features that provide a stable platform for biometric sensors, GPS, and processors on the garment body. Fit of garment body 52 may be athletic, similar to, in certain embodiments, an undershirt worn by a soldier or professional football player. In some embodiments, garment body 52 includes fabric enhancements such as, but not limited to, improved moisture wicking, improved thermal management, and/or muscle group support.

In embodiments with garment body 52 being a shirt body, the garment body may be made available in a number of sizes similar to, but not limited to, standard American sizing. For example, garment body 52 may be available in full and half sizes ranging from size 3 to size 8. A size 3 may be the equivalent of an extra, extra small (XXS) and an 8 may be similar to an extra, extra, extra large (XXXL). In certain embodiments, garment body 52 is form fitting and snug to more accurately measure physiological responses. Thus, in such embodiments, 11 (or more) available sizes may be provided to ensure a form fitting fit on the user.

In some embodiments, garment body 52 is a unisex garment body. Garment body 52 may be fitted based on torso length relevant to chest wall circumference while the garment body is constructed from an elastic material. Fitting and constructing garment body 52 in such manners may allow the garment body to be made unisex, which may make manufacturing, shirt selection, distribution, and inventory of garments more manageable.

In certain embodiments, garment body 52 is form fitting and designed to be worn for prolonged periods of time. Garment body 52 may be designed to fit and be worn like a typical athletic garment. For most typical embodiments, garment body 52 may not need special fitting for the user. Garment body 52 may be form-fitting to allow the garment body to properly collect data from an individual wearer of the garment body (e.g., the user). In some embodiments, a sizing chart is provided to an individual with garment body 52 (or distribution materials for the garment body) to provide a recommendation for sizing of the garment body. Recommendations for sizing may correspond to, for example, chest measurements of the individual or other measurements of body parts of the individual intended for wearing of garment body 52 (e.g., arm diameter, leg diameter, etc.). The sizing process may be a process similar to the process for effectively fitting a high-end backpack or daypack, common in the outdoor retail space. In some embodiments, garment body 52 may be worn under other equipment for prolonged periods of time (e.g., under football pads) or the wearer may have a unique body shape for which a specially-made garment body is needed.

Garment system 50 may include garment body 52 and multiple additional components. In certain embodiments, garment system 50 includes a heart rate monitor (not shown), respiration/skeletal position monitors 116, accelerometers 130, GPS/WWAN component 134, processor 114, a cellular/satellite transceiver (not shown), a low frequency receiver/transceiver system (not shown), kinetic power modulator 138, and generators 136. These components may be attached to or embedded in garment body 52. A dashboard application (e.g., an application on a mobile device) may also be associated with garment system 50. As shown in FIGS. 1 and 2, wiring may couple one or more of the components on garment body 52.

In certain embodiments, processor 114 provides processing of information acquired through various sensors/components on garment body 52. Processor 114 may process the acquired information (e.g., raw data from sensors/components) to generate new information. Processor 114 may transmit the information using the cellular/satellite transceiver and/or the low frequency receiver/transceiver system. Transmitted information may include either processed information and/or raw data information. In some embodiments, processor 114 includes memory for storing the information and transmitting the information at a later time. For example, processor 114 may transmit the information using a burst transmission at a specified time.

In some embodiments, the cellular/satellite transceiver and/or the low frequency receiver/transceiver system are attached to or part of processor 114. In some embodiments, the cellular/satellite transceiver and/or the low frequency receiver/transceiver system are separated from processor 114 in garment body 52. In some embodiments, antennas for either a satellite, a cellular, or another receiver/transceiver are integrated into garment body 52. For example, the antennas may be flexible, flat antennas integrated into garment body 52. Integration of the antennas may include sewing or embedding the antennas into garment body 52. The antennas may include small circuit boards using lightweight materials that provide fast data transfer rates.

In some embodiments, GPS/WWAN component 134 includes the cellular/satellite transceiver and/or the low frequency receiver/transceiver system. In some embodiments, the cellular/satellite transceiver and the low frequency receiver/transceiver systems are redundant systems (e.g., one system is capable of operation if the other system is not operable or transmission using the system is not available).

In certain embodiments, the low frequency receiver/transceiver system is used to create an ecosystem around garment system 50. For example, the low frequency receiver/transceiver system may incorporate a low frequency system such as Bluetooth or Bluetooth Smart. Other communication protocols may also be used such as, but not limited to, ANT+, Wi-Fi, LiFi, and SATCOM. Using such technology may provide for the addition of third-party hardware for extended biofeedback response capabilities. Some possible hardware concepts include, but are not limited to, glasses to track movement and pupil dilation, wristbands to monitor skin conductivity and temperature, ambient temperature sensors, and DTR (deep tendon reflex) monitoring. In some embodiments, the low frequency receiver/transceiver system includes small transmitters and receivers capable of moving large quantities of data and smaller package sizes over greater distances. The low frequency receiver/transceiver system utilize protocols to include a wide variety of third-party hardware. In some embodiments, submersible technology may be incorporated in the low frequency receiver/transceiver system.

In certain embodiments, an application is associated with garment system 50. For example, as described above, a dashboard application (e.g., an application or module on a mobile device or other electronic device) is associated with garment system 50. Processor 114 may communicate with the device to send/receive data between the application and garment system 50. The application associated with garment system 50 may provide simultaneous review of all biometric information as well as complementary information generated by the processing of acquired data (e.g., algorithmic manipulation of acquired data). The application may allow for the management, utilization, and near real-time review of gathered data regardless of the physical location of the device relevant to garment system 50.

In some embodiments, the application associated with garment system 50 may be a native iOS or Android application as well as a web platform. The dashboard application may access a remote server associated with garment system 50 (e.g., through a secure Internet connection). The application may provide capability for the passing of information and system management tools between garment system 50 and the remote server. This setup may allow for wireless firmware updates and remote diagnostic capabilities. Live "over-the-wire" firmware updates may occur as enhancements are made and the garment application may be updated as improvements occur. Initially, the garment application may allow for the measurement and viewing of all biometric processes being monitored and GPS location. In some embodiments, garment system 50 may include control capabilities such as VO2 Threshold, Tidal Volume, WAN locating, 3D Thoracic wall movement diagramming, third-party apps, etc.

In some embodiments, a heart rate (HR) monitor is incorporated in garment body 52. The HR monitor may function utilizing decoding algorithms and three lead EKG equivalent monitoring straps. In some embodiments, the HR monitor may integrate a 12 lead EKG equivalent monitor. The HR monitor may, however, integrate any number of leads in an EKG equivalent monitor. The HR monitor may stream pulse rate to processor 114, which may run the data through multiple algorithms developed and offered as a package. The algorithms offered may provide, but not be limited to, the following outputs: BPM (beats per minute), HRR (heart rate reserve), stress response, and HRV (heart rate variability).

In some embodiments, the HR monitor is integrated into the material of garment body 52. The HR monitor may be, for example, a standard heart rate monitor that circumnavigates either a portion of the user's chest or a portion of the user's body adjacent the chest. The HR monitor may utilize three lead EKG equivalent monitoring techniques using electrically conductive pads. The HR monitor may be positioned anatomically under the breast line of the user and over the top of the xiphoid process (in proximity to dotted line 140 found in FIG. 1). The HR monitor may track pulse rate (and/or other information) in near real-time and may transmit the information via hardwire to processor 114.

In certain embodiments, the HR monitor includes a pulse oximeter. The pulse oximeter may be used to assess SpO2 (blood oxygen saturation) levels in the wearer. In some embodiments, the pulse oximeter is separate from the HR monitor on garment body 52. Measurements of SpO2 from the pulse oximeter may be combined with other data to provide an assessed condition of the wearer of garment body 52.

The HR monitor may also include low-frequency wireless technology such as, but not limited to, Bluetooth Smart. The Bluetooth Smart or similar technology may allow for the heart rate to be transmitted in near real-time to a third-party device or monitoring tool. The third-party device or monitoring tool may include devices/tools such as, but not limited to, an electronic device including an application (e.g., a mobile device with a dashboard application), deep tendon reflex monitoring cuffs, pedometers, glasses utilized to track multiple periods of vision, eye movement, and focal points, skin conductivity monitors, skin temperature monitors, and atmospheric monitors. Wireless transmissions may be secondary to hardwired transmissions through a hardwired connection to processor 114. The contact pads for the heart rate monitor may be rubberized and fully encapsulated to ensure that the unit is watertight.

In certain embodiments, battery 132, shown in FIG. 2, is used to provide power for the HR monitor (and other components) of garment system 50. In certain embodiments, battery 132 is a flexible, thin battery that is non-combustible. In some embodiments, battery 132 is a flexible battery distributed through a portion of garment body 52. Battery 132 may be removable from garment body 52 (e.g., for replacement and/or recharging of the battery).

In some embodiments, the HR monitor is coupled to battery 132 via a wired connection. In some embodiments, the HR monitor may include updated firmware and technology upgrades including more efficient monitoring, three-dimensional sonography, target specific ultrasound, and more frequent data transmissions.

In certain embodiments, garment system 50 includes a magnetic respiratory monitor. The magnetic respiratory monitor may be used to measure chest wall and/or abdominal movement (e.g., expansion and contraction). In certain embodiments, the magnetic respiratory monitor measures chest wall and abdominal movement at twelve points on the body, with six points being on a first side of the body and six points being on a second side of the body. Four leads may be placed at relevant points along the thoracic wall to monitor the linear movement of the related space along a linear plane. Two leads may be placed on the lateral aspect of the abdominal wall to monitor for diaphragmatic breathing. The respiration rate, frequency, and depth may be transmitted over wire in real-time to processor 114. Processor 114 may process the information through a series of algorithms to determine results such as, but not limited to: respiration depth, respiration quality, respiration rate, respiratory rhythm, and relevant chest wall and abdominal movement (symmetric, asymmetric, variance, etc.).

Figure 3:
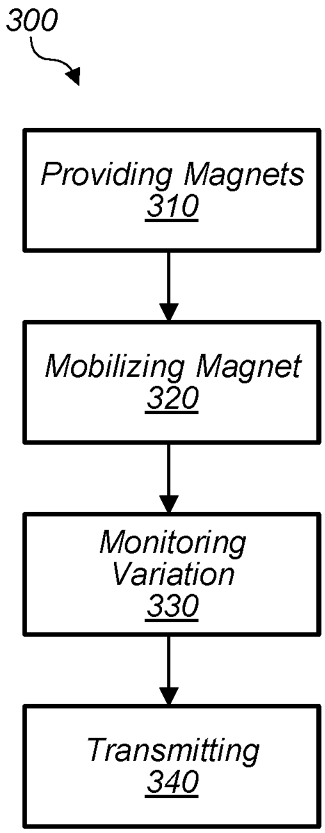
FIG. 3 displays an embodiment of a method.

FIG. 3 displays an embodiment of method 300. Method 300 may be used for monitoring an individual using a magnetic respiratory monitor in accordance with embodiments described herein. Method 300 may include providing magnets 310. In certain embodiments, two magnets are provided. In some embodiments, a first magnet is a static magnet. In 320, a second magnet may be mobilized in the vicinity of the static magnet. In 330, a magnetometer may monitor the variation in magnetic force applied to the static magnet by the mobilized magnet. In certain embodiments, the mobilized magnet is attached to the mediastinal breastplate of garment body 52. The position of the mediastinal breastplate may be represented by position 142, shown in FIG. 1.

Magnetic variance may occur on inspiration and expiration as the magnet attached to the breastplate moves away from the static magnet during inspiration and back towards the static magnet during expiration. In 340, the variance in force may be transmitted by the magnetometer to the processor (e.g., processor 114). The number of times the variances are recorded over a period of time may be identified as the number of respirations in that period. In certain embodiments, the pair of magnets involved in method 300 are encapsulated in a thin waterproof tube in conjunction with the magnetometer. The static magnet may be glued in place to the interior of the watertight tube. Each magnetic device may consist of a magnetometer, a static magnet secured to the interior of the tube, a mobile magnet inserted into the interior of the tube, a watertight tube, and a cable attachment to the breast plate.

There may be a plurality of magnetic devices distributed throughout garment body 52. For example, in one embodiment, there may be twelve magnetic devices distributed throughout garment body 52. In some embodiments, four devices are located over the left lateral aspect of the thorax and four devices are located over the right lateral aspect of the thorax. In some embodiments, two devices are located over the left anterolateral aspect of the abdomen and two devices are located over the right anterolateral aspect of the abdomen. In some embodiments, a magnetic respiratory monitor may be placed within garment body 52 on each side of the garment body. The monitors may correlate with an upper chest wall of an individual so that breathing patterns in these two areas may be monitored. In some embodiments, the length of the tube may align with an outward axis of breathing of the individual so that the magnets move along this axis and provide useful measurable results. In some embodiments, garment system 50 includes magnetometry that does not require actual moving magnets, uses smaller integrated systems, and provides faster, more reliable reads.

In some embodiments, the magnetometer includes standard magnetometer components that are capable of measuring at least one of the following: the magnetization of a magnetic material and the strength and/or direction of a magnetic field at a point in space. In some embodiments, a sensor of the magnetometer is positioned within the magnetic field found within or in the vicinity of the tube housing the static magnet and the mobile magnet.

In some embodiments, garment body 52 is worn in conjunction with a belt. The belt may include a magnet and magnetometer setup as described above with the tube aligning along an axis perpendicular to the length and width of the belt. The belt may, when garment body 52 is worn by an individual, circumnavigate the pelvic region of an individual and may carry out at least one of two tasks: 1) keep the garment in place if an individual is wearing the garment and 2) measure the pelvic positioning of an individual. In some embodiments, the belt may be positioned over the iliac crests of the pelvis.

In some embodiments, garment body 52, in the form of a shirt, includes a waistband sewn within a hem of a shirt. The waistband may, when garment body 52 is worn by an individual, circumnavigate the pelvic region of the individual. The waistband may comprise a magnet and magnetometer setup as previously described with the tube aligning along an axis perpendicular to the length and width of the waistband. The waistband may measure the pelvic positioning of an individual when the individual is wearing garment body 52. In some embodiments, the waistband includes an elastic material. In some embodiments, the waistband is positioned over the iliac crests of the pelvis.

Figure 4:
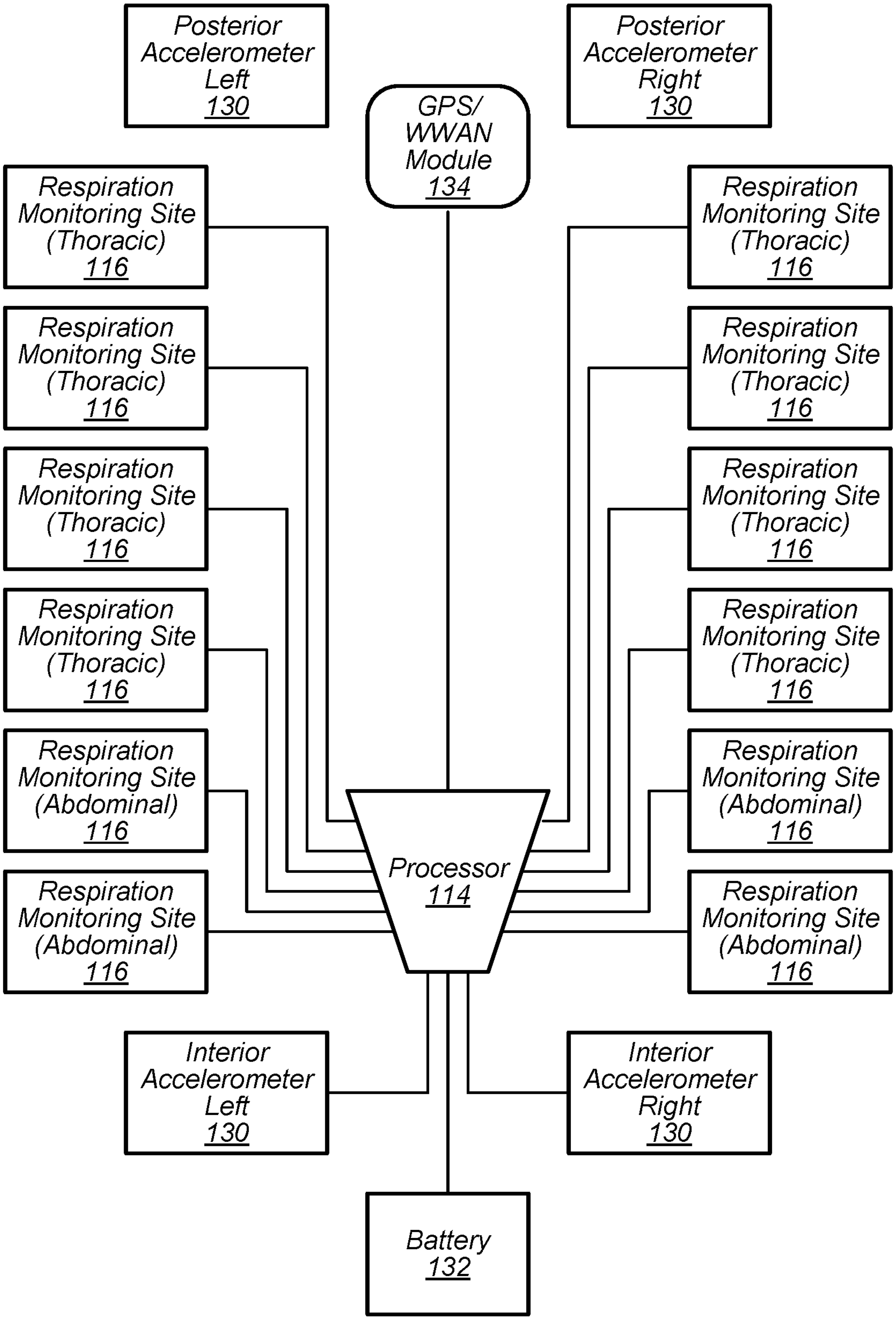
FIG. 4 displays a diagram depicting an embodiment of a wired framework of a garment system.

FIG. 4 displays a diagram depicting an embodiment of a wired framework of garment system 50. In certain embodiments, garment system 50 integrates up to twelve primary components. In certain embodiments, garment system 50 includes processor 114. Information generated by biometric sensors, Bluetooth extensions, GPS signals, and any other general feedback provided through the garment system may be processed within the garment system using processor 114. Processed data packets may be transmitted via uplink to a server associated with garment system 50 and then made available in near real-time to a dashboard/application, as described herein. The mechanism of processing information on board garment system 50 may allow for the continuous cycling and evaluation of data even in the event of uplink loss. This may be critical in high-conflict/shielded areas such as areas near power-lines, around dense foliage, or building cover. Once communication with the server is re-established, burst transmissions may occur in order to move as much information to the server, and then out to the users, as fast as possible. In some embodiments, processor 114 provides a fast processor (e.g., parallelized multicore processing) in a smaller chip size with more powerful, deeper evaluation of biometric feedback data.

Garment system 50 may include a wireless monitoring system that provides testing typically reserved for the lab. Processor 114 may be wired or wirelessly connected with a plurality of respiration monitoring sites 116. Using respiration monitoring sites 116 placed at thoracic and abdominal areas, garment system 50 may provide monitoring for respirations, heart rate, and thoracic movement along with relevant conjoined data. Garment system 50 may allow for the integration of Bluetooth Smart enabled peripheral monitors. The wireless capabilities of garment system 50 may also provide channels for updating and expanding of the garment system.

In certain embodiments, garment system 50 includes eight thoracic respiration monitoring sites 116 and four abdominal respiration monitoring sites 116 (both generally denoted as respiration monitoring sites 116). A rechargeable battery 132 may be connected to processor 114. Battery 132 may be encased in a waterproof shell that is resistant up to 100 meters of water or greater. The configuration of battery 132 may depend on the variation of garment system 50. For example, a commercial version of garment system 50 may utilize an integrated battery 132 that requires that the garment system to be returned to a company for a swap out of the battery once the battery has exceeded life expectancy. In some embodiments, an accessible version of garment system 50 may utilize a removable battery for battery 132 that allows for emergency swap out, field servicing, and/or swaps on prolonged operations (such as in the military). The estimated standby time for garment system 50 without kinetic influence or charge may be about 10-15 days, which may reduce or eliminate the possibility of power sapping.

In certain embodiments, garment system 50 includes a plurality of accelerometers 130. Accelerometers 130 may be strategically integrated/placed in garment body 52. The integration of accelerometers 130 may provide additional data acquisition for garment system 50. Accelerometers 130 may, for example, provide the location of garment system 50 relevant to perpendicular and/or the ground and thus provide the body position of the wearer relevant to perpendicular and/or the ground. Providing body position may allow an evaluator to determine the activity of the wearer (running versus biking, versus swimming, etc.). Accelerometers 130 may identify position relevant to the perpendicular in conjunction with being relevant to each other. Accelerometers 130 may further determine torso and limb movement associated with mobility. Accelerometer 130 may further be used to determine the quality of specific movements.

In some embodiments, garment system 50 includes four accelerometers 130: a left posterior accelerometer, a right posterior accelerometer, a left anterior accelerometer, and a right anterior accelerometer. Accelerometers 130 may collect information on the movement of an individual including the direction of movement, the speed of movement, the duration in which a movement takes place, and the smoothness of the movement. This information may be provided to processor 114 and stored on a memory in connection with the processor. Processor 114 may correlate the data with sample data that may represent a specific activity. This correlation may allow garment system 50 to tell what type of activity an individual is doing, how well the individual is performing an activity, and how well the individual is doing (health-wise) during the activity.

In some embodiments, garment system 50 includes one accelerometer 130 over the posterior superior lateral aspect of the left scapula, one accelerometer 130 over the posterior superior lateral aspect of the right scapula, one accelerometer 130 placed over the left anterior superior medial aspect of the ischial crest, and one accelerometer 130 placed over the right anterior superior medial aspect of the ischial crest. Each accelerometer 130 may relay information independently to processor 114 so that the individual accelerometers' 130 positions relevant to perpendicular and/or the ground can be measured as well as variations to perpendicular to the ground. Each unit may measure its relative position, speed, and momentum respective to every other unit. This information may also be sent to processor 114 by each individual accelerometer 130. The combined data in aggregate from the accelerometers 130 may provide a three-dimensional digital view of the body in motion. In some embodiments, the size and/or number of accelerometers 130 may vary in garment system 50. Additionally, accelerometers 130 and/or processor 114 may include upgraded hardware and/or software to provide more accurate and faster data aggregation.

In some embodiments, accelerometers 130 include, or are included as part of, inertial measurement units (IMUs). Inertial measurement units may be used to assess the bodies physical position in a three-dimensional space as well as complex motion. The use of inertial measurement units may provide near real-time mapping of complex motions including rotation, flexion, and extension. Inertial measurement unit data may be used in combination with other data (e.g., GPS data) to provide a three-dimensional image of the wearer's body in space relative to other objects (e.g., a real-time tracking image).

In certain embodiments, processor 114 is connected to GPS/WWAN component 134. GPS/WWAN component 134 may include a GPS monitor and/or a WWAN monitor. The GPS monitor may be stacked or swapped with the WWAN monitor for indoor movement tracking in a 3D space. In some embodiments, the purpose of GPS/WWAN component 134 is to determine the wearer's physical position in a real-world environment. In some embodiments, the ping rate for GPS/WWAN component 134 may be one second intervals (e.g., the closest to constant position streaming currently available).

In some embodiments, GPS/WWAN component 134 may be located along the spinal column over the C5. GPS/WWAN component 134 may be small in size and may be low profile. GPS/WWAN component 134 may utilize an integrated antenna. For high standard versions (e.g., military versions) of garment system 50, an elongated, flexible, and flat GPS antenna may be integrated into garment body 52. The GPS component of GPS/WWAN component 134 may be utilized to track the physical location of the body in a real-time environment. For certain purposes (e.g., military purposes), GPS/WWAN component 134 may be capable of utilizing WWAN to track a wearer through an interior environment. WWAN integration may afford observers utilizing the app or web dashboard to track the garment's wearer in near real time on a map overlay. In some embodiments, GPS/WWAN component 134 includes small units that provide good satellite tracking, fast locking, and good transmission through dense cover.

Figure 5:
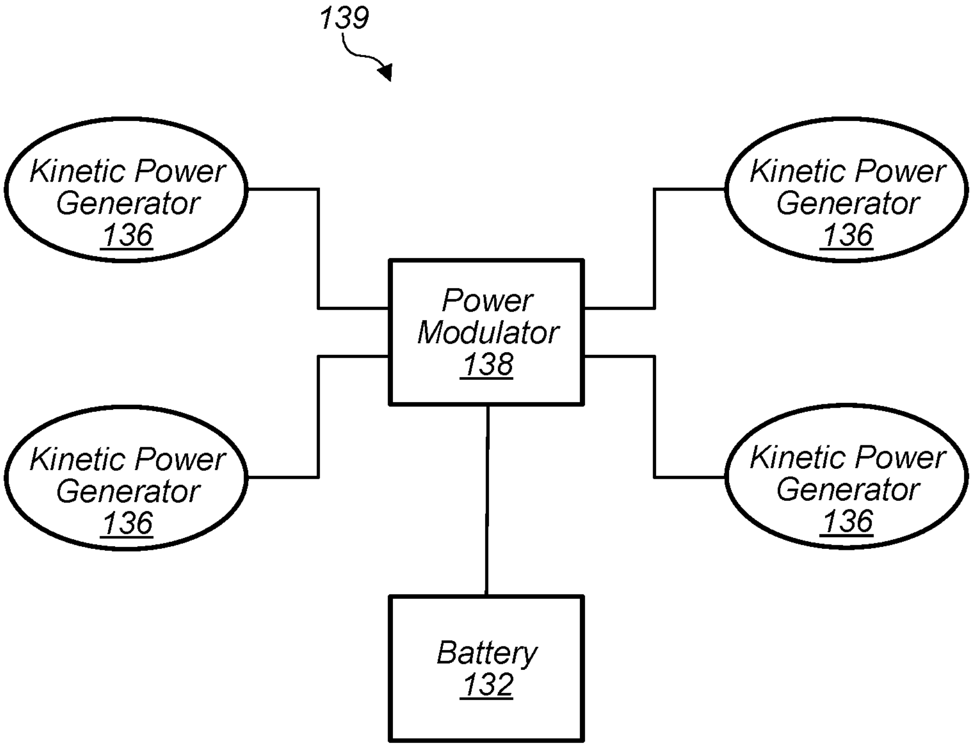
FIG. 5 displays a diagram of an embodiment of a kinetic power module setup.

FIG. 5 displays a diagram of an embodiment of kinetic power module setup 139. In certain embodiments, kinetic power module setup 139 is included in garment system 50. Kinetic power module setup 139 may allow garment system 50 to provide a low frequency wireless enabled wearable utilizing at least one power generator, magnetic respiratory monitor, and onboard processor 114. The method of acquiring, processing, and transmitting biometric feedback data using garment system 50 may allow for the complete physical evaluation of a wearer without being harnessed to a treadmill, spirometer, and ECG machine while being isolated to a lab outside of an active real-world environment. Thus, garment system 50 may take the guess work out of live, real-world performance and stress response.

In certain embodiments, kinetic power module setup 139 and garment system 50 include at least one integrated kinetic power generator 136 that allows for the garment system to continuously charge while the wearer is in motion. Continuous charging may allow battery 132 to only deplete when the body is static. Charging using kinetic power module setup 139 may increase the battery life and decrease the requirement for charging. The kinetic charging may allow garment system 50 to be used for long duration activities. Long duration activities may include, for example, combat operation scenarios such as foot patrols, Direct Action Operations, and/or training exercises spanning multiple days in the field. Long duration activities may also include commercially viable activities such as triathlons and endurance races. In some embodiments, kinetic generators 136 may be diffuse kinetic chargers.

Kinetic generators 136 may be integrated into garment body 52, as shown in FIGS. 1 and 2. Kinetic generators 136 may include multiple micro-kinetic power generators that are located throughout garment body 52. In certain embodiments, kinetic generators 136 are placed in strategic areas (e.g., areas with high movement such as the shoulders and/or hips). As shown in FIG. 5, each kinetic generator 136 may be coupled to power modulator 138. Energy generated in each kinetic generator 136 may be throttled through power modulator 138 to trickle charge the garment's battery 132. Power modulator 138 may be capable of trickle charging battery 132 from the charge of a single kinetic generator 136 or all kinetic power generators 136 simultaneously. This may be necessary because in certain body positions, or during certain activities, there may be limited motion through all or some of the upper extremities and thus regions of garment body 52. Power modulator 138 may be directly wired to the battery 132 in order to provide the charge/trickle charge. In some embodiments, kinetic power module setup 139 may be based on the Seiko-type kinetic power generation system that has been utilized in watches since the early 80s. In some embodiments, kinetic power generators 136 may include smaller generators capable of generating more power from less movement. In some embodiments, kinetic power generators 136 may incorporate organic solar paneling woven into the garment material of garment body 52.

Figure 6:
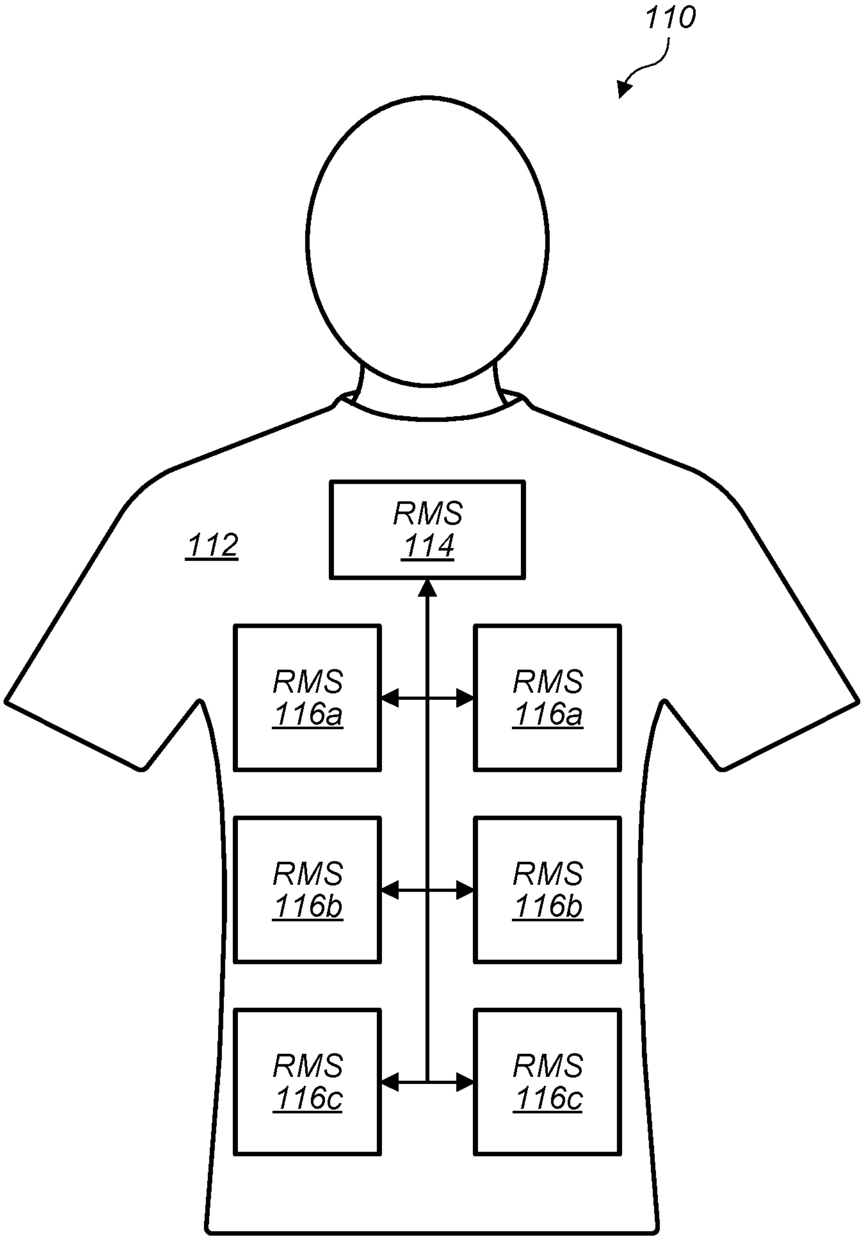
FIG. 6 illustrates an embodiment of a respiratory monitor sub-system.

FIG. 6 illustrates an embodiment of respiratory monitor sub-system 110. Respiratory monitor sub-system 110 may be integrated into shirt 112 (e.g., garment body 52) and may include processor 114 and multiple instantiations of respiration monitoring site ("RMS") 116, i.e., RMS **116*a*-116*f*. Each RMS 116 may be connected to processor 114 via a serial bus. During operation, each RMS 116 may sense movement, as described below, and provide a corresponding digital output that is a function of the detected movement. In some embodiments, each RMS 116 output is latched and scanned serially back to processor 114 where it is available for further analysis or processing. In other embodiments, the digital data provided by each RMS 116 may be provided to processor 114 along a parallel bus. In some embodiments, respiratory monitor sub-system 110 may not include processor 114**.

Figure 7:
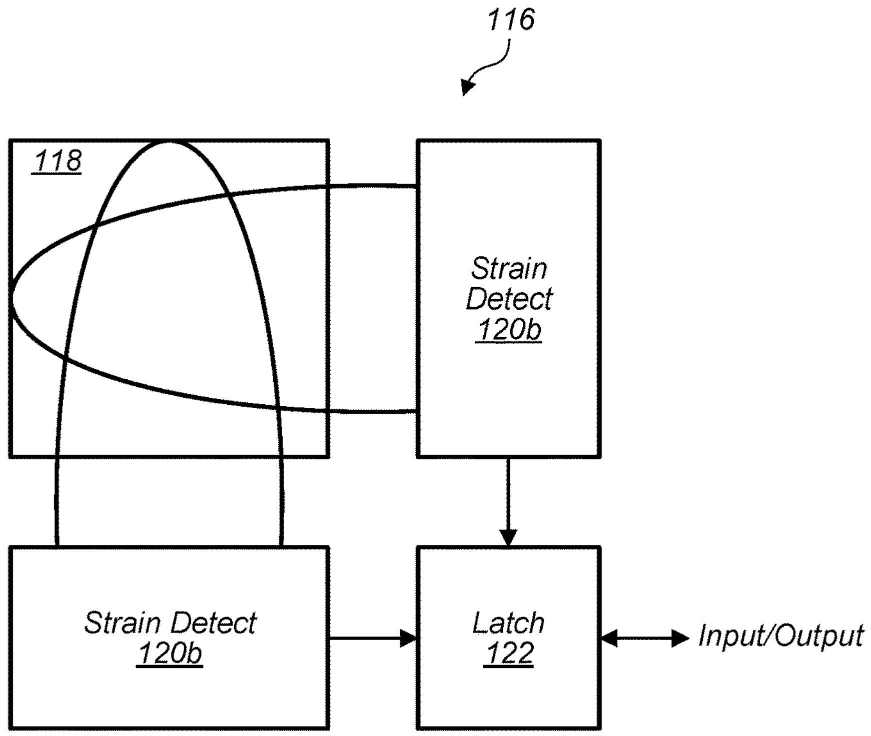
FIG. 7 illustrates another embodiment of a respiratory monitor sub-system.

FIG. 7 illustrates an embodiment of RMS 116. RMS 116 may include conductive elastomer ("CE") panel 118, multiple instances of strain detection unit 120 (e.g., strain detection units **120*a*-120*b*), and latch 122. CE panel 118 may include at least 2 strips of material (e.g., strands or fibers of a conductive elastomer), one substantially in the horizontal direction, and one substantially in the vertical direction. CE panels 118 may be integrated into shirt 112 (e.g., garment body 52**) over areas that are affected during the respiratory process; for instance, over the rib cage and upper abdomen. When inhalation and exhalation occur, the material stretches, expanding and contracting with body motion, i.e., thoracic expansion and contraction while breathing.

As is known, the resistance of the conductive elastomer fibers or threads is given as:

$$R=(p*l)/A;$$

where R represents the resistance, p represents electrical resistivity (Ω·m), A represents the cross-sectional area in $m^2$, and l=length of the conductor in m. According to this relation, when the area of the conductive elastomer decreases, its resistance increases. Deflection, i.e., expansion and contraction, of the conductive elastomer results in a decrease in the cross-sectional area and a concomitant change in the resistance of the conductive elastomer.

Strain detection units 120*a* and 120*b* may detect the changes in the resistance of the conductive elastomer that results from the expansion and contraction of the strands that accompany inhalation and exhalation. Latch 122 may capture the results of the detection performed by strain detection unit 120 and provide the captured data to processor 114 by way of the aforementioned serial or parallel bus.

Figure 8:
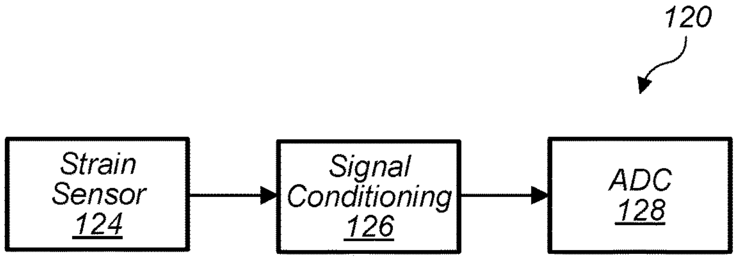
FIG. 8 illustrates an embodiment of a strain detection unit.

FIG. 8 illustrates an embodiment of strain detection unit 120. Strain detection unit 120 may include strain sensor unit 124, signal conditioning unit 126, and analog-to-digital converter ("ADC") 128. During operation, strain sensor unit 124 may detect the changes in resistance resulting from the deflection of the conductive elastomer strands due to inhalation and exhalation. The results from strain sensor unit 124 may be provided to signal conditioning unit 126, where the resulting signal or signals are, for example, amplified and any DC offset is removed. The conditioned signal may be provided to ADC 128 where the signal is converted into a digital output. ADC 128 may be a simple 1-bit ADC, a more complex 24-bit ADC, or something in between, depending upon the application and the needs of the system.

Figure 9:
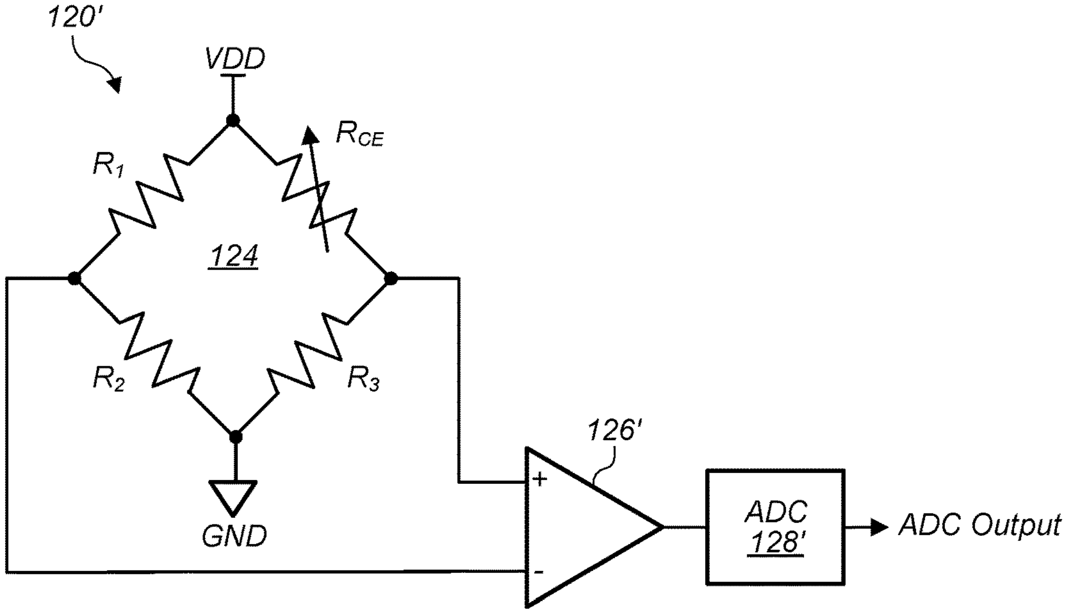
FIG. 9 illustrates another embodiment of a strain detection unit.

FIG. 9 illustrates another embodiment of strain detection unit 120'. Strain detection unit 120' may include Wheatstone bridge 124', amplifier 126', and ADC 128'. Wheatstone bridge 124', as is known, is often used to accurately measure small changes in resistance of a strained medium, converting the changes in resistance into a voltage that can be amplified by amplifier 126' and converted to a digital output by ADC 128'. Wheatstone bridge 24' includes 4 resistors R1, R2, R3, and RCE, where RCE is the resistance of the conductive elastomer. When all four resistors in Wheatstone bridge 124' are equal, the bridge may be perfectly balanced and the output voltage is equal to zero. But when any one or more of the resistors change value by only a fractional amount, the bridge produces a measurable voltage. The output voltage of the Wheatstone bridge 124' is given by:

$$V_{out}=V_{DD}((R_2/(R_1+R_2))-(R_3/(R_{CE}+R_3))).$$

Thus, when the resistance of the conductive elastomer, illustrated here as RCE, changes, the output voltage provided to amplifier 126' reflects that change as a change in voltage which is then conditioned and amplified by amplifier 126'. The amplified signal is then converted to a digital output by ADC 128'. As before, ADC 128' may be a simple 1-bit ADC, a more complex 24-bit ADC, or something in between, depending upon the application and the needs of the system.

Figure 10:
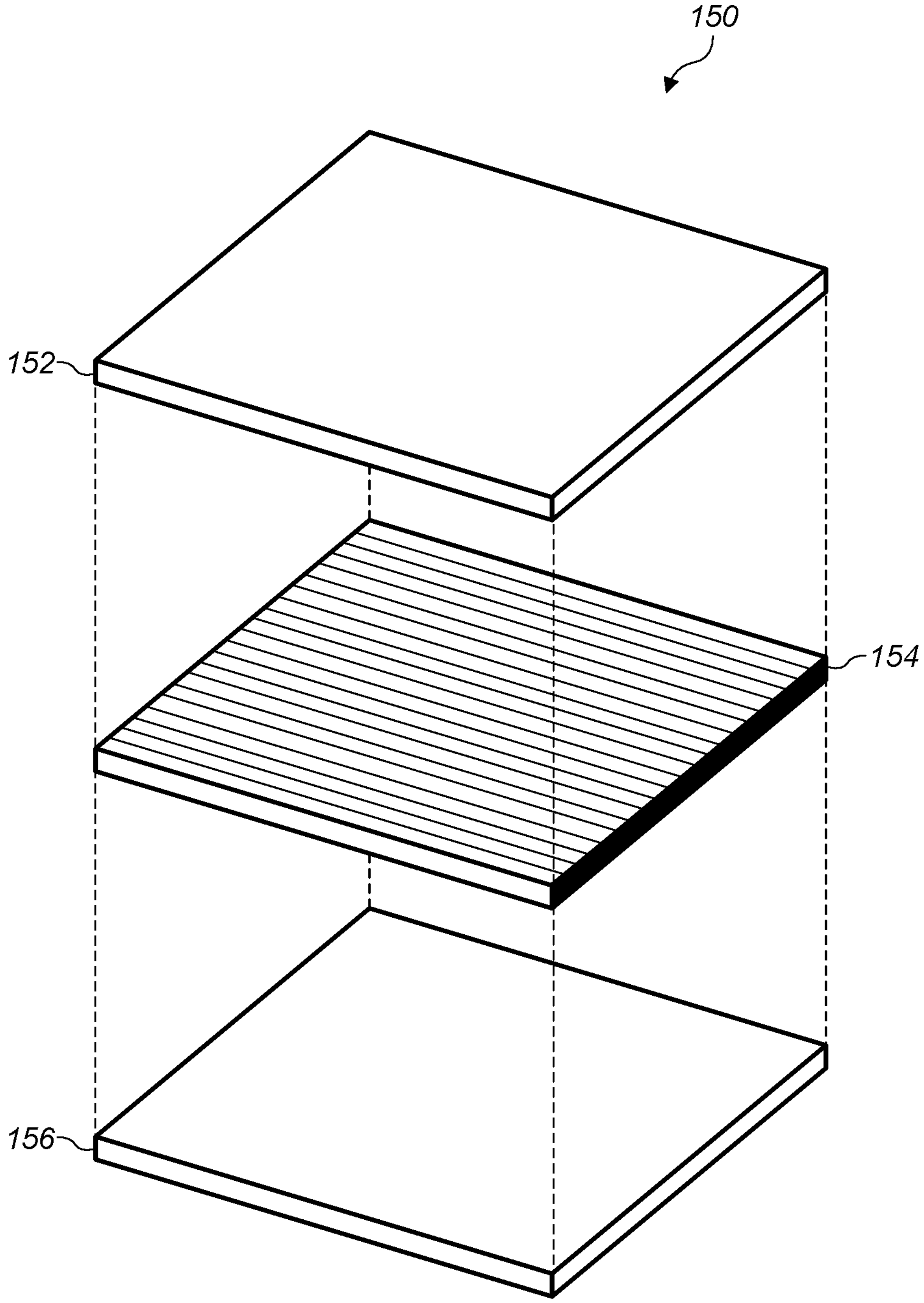
FIG. 10 displays a side layer view of an embodiment of a multi-layer elastic conductive fabric utilized in a garment body.

FIG. 10 displays a side layer view of an embodiment of multi-layer elastic conductive fabric 150 utilized in garment body 52. Fabric 150 may include top layer 152, bottom layer 156, and midsection 154. In embodiments where garment body 52 is a shirt, the garment body may include form-fitting fabric that has an open interior defining a torso. Garment body 52 may, however, include any form-fitting fabric with an open interior for any body part (e.g., arm or leg).

In certain embodiments, bottom layer 156 is a conductive elastic fabric layer. Bottom layer 156 may, for example, include conductive flexible fibers. In some embodiments, bottom layer 156 includes a rubberized conducive material, such as, but not limited to a metal rubber. Metal rubber may provide an ideal set of properties including elasticity and conductivity. When an individual is wearing garment body 52, bottom layer 156 may be adjacent the individual's skin. Bottom layer 156 may receive a natural current from the individual's skin that may be transmitted throughout the bottom layer. In certain embodiments, this natural current may be measured by one or more RMS 116, which may output data that is analyzed to show how an individual is positioned or is breathing. In some embodiments, a current from a component of garment body 52 may provide a current that is supplied to bottom layer 156 and one or more RMS 116. In some embodiments, the current supplying component may be battery 132.

Midsection 154 may be an insulative fabric such as, but not limited to, a woven textile including insulative fibers. In some embodiments, midsection 154 may include cross-linked material. It should be noted that the insulative fibers of the woven textile may be adjacent bottom layer 156 so that the bottom layer may carry a charge from one point to another without midsection 154 interfering with the current passed through the bottom layer. Top layer 152 may include an elastic fabric such as, but not limited to spandex and Lycra. In certain embodiments, midsection 154 is adhered to the top and bottom layers 152,156 via an adhesive polymer. In some embodiments, the woven textile of midsection 154 is woven to at least one of the top and bottom layers 152,156. In some embodiments, the elastic conductive polymer may exhibit characteristics similar to a metal rubber.

Figure 11:
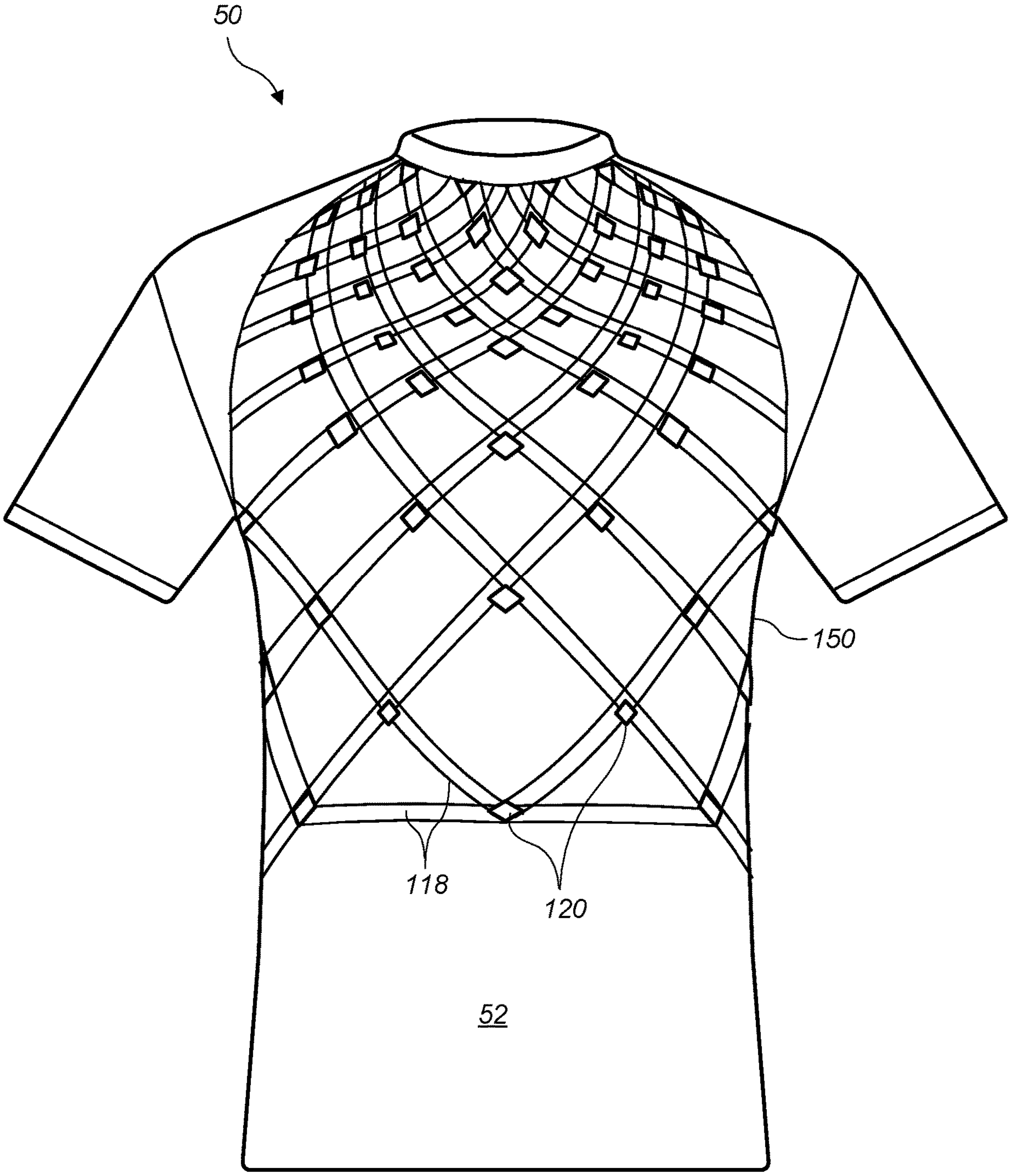
FIG. 11 displays a front view of an embodiment of a respiratory monitoring system engrained within a garment body.

FIG. 11 displays a front view of an embodiment of a respiratory monitoring system engrained within garment body 52. As shown in FIG. 11, multi-layer elastic conductive fabric 150 may include a definite width that may be confined within a length from a first detection unit 120 to a second detection unit 120. In some embodiments, as shown in FIG. 11, multi-layer elastic conductive fabric 150 may alternatively be designated as "panel strips". A plurality of panel strips may make up a framework splayed across garment body 52 in diagonal patterns to provide conductivity to a plurality of detection units 120 found on a large portion of the garment body. These panel strips may be woven and/or stitched to garment body 52 itself. At each contact point/overlap, detection unit 120 may be located to create a data packet on the current being passed at that specific monitor. The data packet may include a time at which a current is measured. Detection units 120 may then send the information to either processor 114 on garment body 52 or an external processor that may store and analyze the data packets received using either a wired or wireless connection (such as those mentioned herein). Using one or more algorithms, processor 114 may output breathing information on an individual wearing garment body 52.

Figure 12:
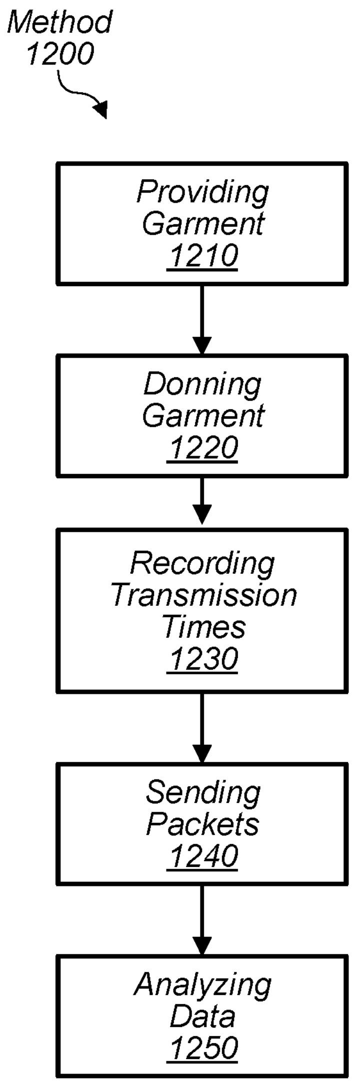
FIG. 12 displays an embodiment of a method for monitoring body functions.

FIG. 12 displays an embodiment of method 1200 for monitoring body functions. Method 1200 may measure functions such as, but are not limited to, inspiration, expiration, skeletal positional quality, and volume of respiration. Method 1200 may utilize any of the embodiments of garment system 50 including a respiratory monitor system and detection units 120. Method 1200 may be utilized in conjunction with the physical movements of the respiratory process.

Method 1200 may include providing garment system 50 to an individual in 1210. The user may don garment system 50 in 1220 and may breathe (perform inspiration and expiration) while wearing garment body 52. While wearing garment body 52, the user's breathing may cause multi-layer elastic conductive fabric 150 of the garment body to elongate and the conductive fibers in the material to become uniformly thinner. As the conductive fibers become thinner, the resistance along the conductive fibers increases. Because of the increased resistance, the transmission time of the electrical signal across the fabric increases. These transmission times may be recorded in 1230 by detection units 120 placed within the garment 50. The material may be incorporated into garment body 52 so that substantially all expansion of fibers is along a linear plane. The recordation of times may then be included in information packets sent 1240 to processor 114 for further analysis in 1250.

Figure 13:
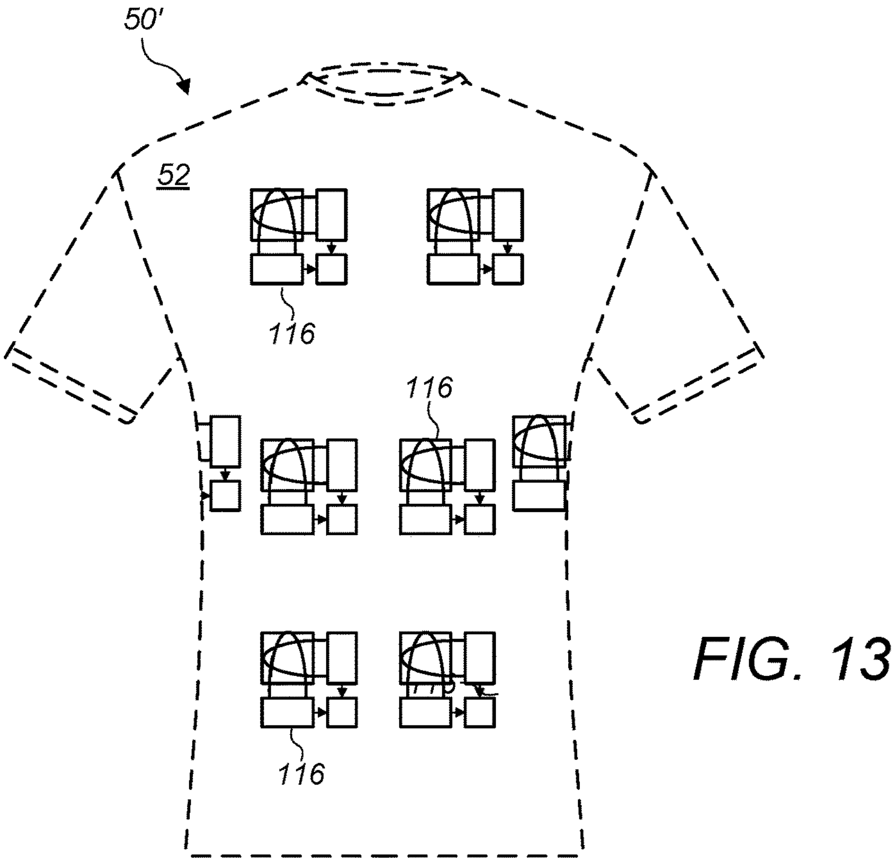
FIG. 13 depicts an anterior view representation of another embodiment of a garment system.
Figure 14:
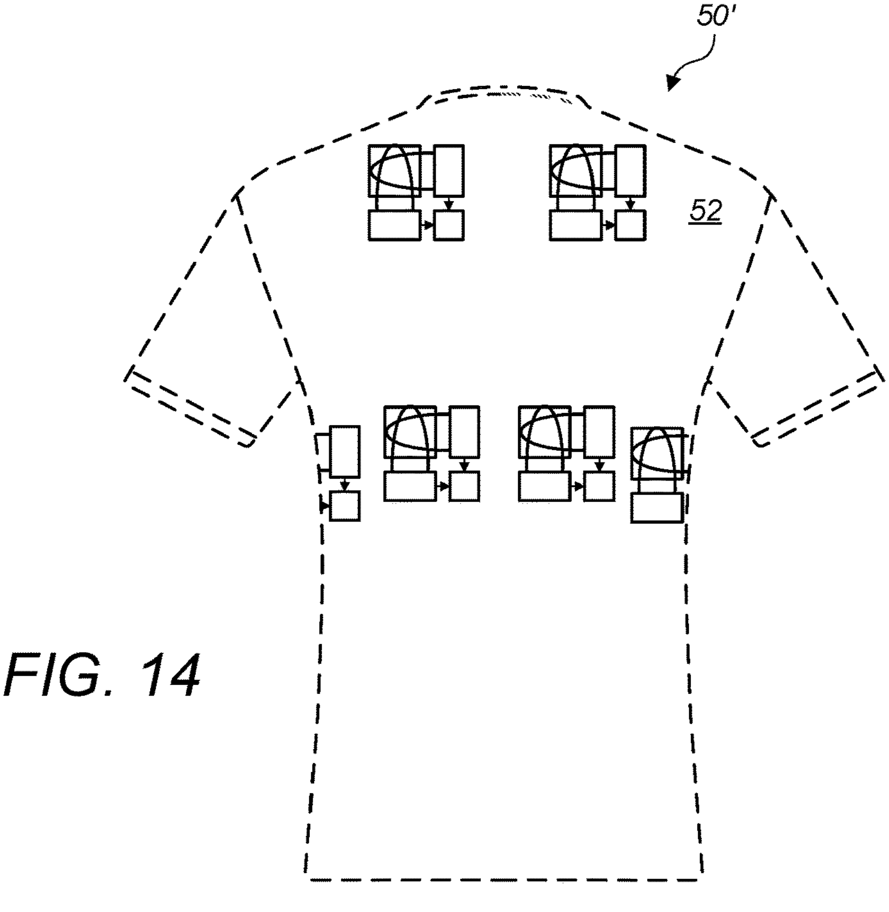
FIG. 14 depicts a posterior view representation of another embodiment of a garment system.

FIGS. 13 and 14 depict another embodiment of garment system 50'. Garment system 50' may include a plurality of RMSs 116 located on the anterior and the posterior of garment body 52. RMSs 116 may be integrally placed to provide sufficient monitoring of an individual's bodily movements, functions, and/or positioning. Garment system 50' may include six RMSs 116 located on the anterior portion of garment body 52, four RMSs 116 located on the posterior portion of the garment body, and two RMSs 116 located right below the armpit portions of the garment body.

Figure 15:
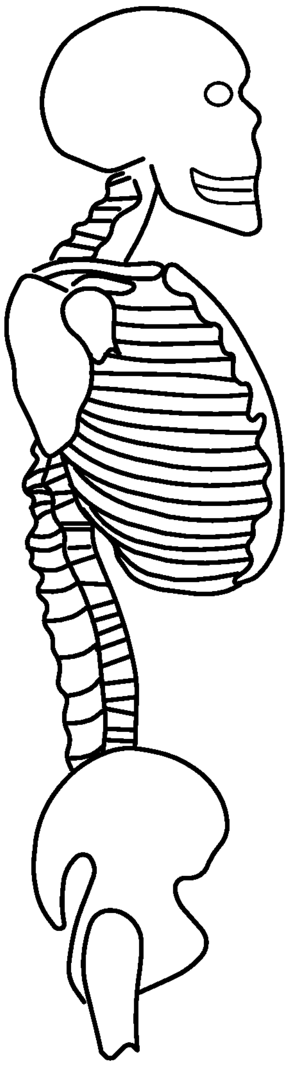
FIG. 15 depicts a side view of an embodiment of a skeleton with a posture characteristic.
Figure 16:
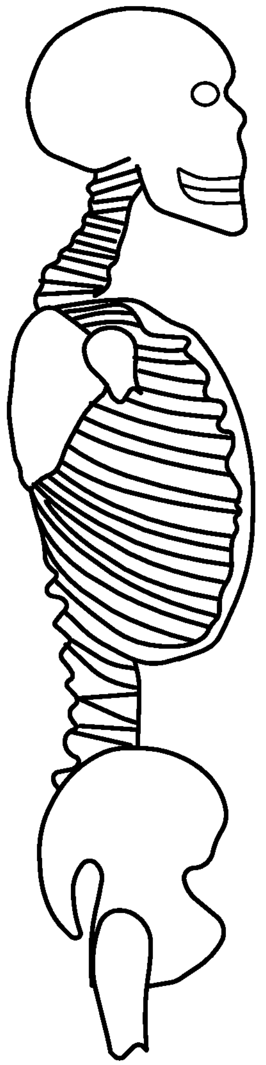
FIG. 16 depicts a side view of an embodiment of a skeleton with an alternative posture characteristic.

FIGS. 15 and 16 depict side views of an embodiment of a skeleton with varying posture characteristics. FIGS. 15 and 16 are reproductions of figures in a presentation by James Anderson, MPT, PRC of the Postural Restoration Institute® entitled "POSTURAL RESPIRATION—An Integrated Approach to Treatment of Patterned Thoraco-Abdominal Pathomechanics" on Aug. 23-24, 2014 in Loveland, Colo. These posture characteristics may be analyzed using RMSs 116 found on garment body 52. Detection units 120 utilized in RMSs 116 may not be just quantitative (like how rapidly someone is breathing or how fast their heart is beating) but may also be qualitative. Garment system 50 may provide a window into how effectively an individual is breathing, what subtle positional factors in their spine and ribcage exist, and what state their autonomic nervous system is in as they train (rest and recover).

The autonomic nervous system (ANS) regulates most of the body's crucial systems like digestive, cardiac, immune and lymphatic systems. Regulation may be achieved via a balanced relationship between two sub-systems, the parasympathetic or "rest and digest" system (PNS) and the sympathetic "fight or flight" system (SNS). Studies on elite performers ranging from Navy SEALs to students taking college entrance exams show that the top performers have the best variance in their nervous systems and are able to baseline most effectively in a restful, parasympathetic state when at rest.

These elite performers are able to spike strongly and immediately into a powerful sympathetic response when needed, and then abruptly drop back into recovery mode between either sets of a tennis match, jumping out of an airplane, or while at home over the weekend. Their heart rates dip more at night during sleep than their lower-performing counterparts, and they hit harder with a more robust "engage threat" response when called upon. Top performers have greater biological power because they only put their foot on the gas at the precise times when it's necessary. Underperformers are essentially working with one foot on the gas and the other on the brake at all times, neither hitting top speed nor slowing down and taking stress off the engine. Variability is availability.

Much of this analysis comes down to breathing and the interplay between respiratory patterns, heart rate, the autonomic nervous system, and the positioning of the spine and ribcage. Garment system 50 may provide near real-time monitoring and dynamic adjustment of all of the above. Breathing is generally misunderstood, predictably inefficient even in well-trained athletes and difficult to monitor without a system such as garment system 50. Breathing is a direct input into the autonomic nervous system (ANS) and drives positioning of the thorax, which is not only crucial for effective performance and the avoidance of injuries, but again directly affects the ANS.

The body has inherent physical asymmetries. For example, the liver is located on the right of the torso, with the heart shifted towards the left side of the chest. The liver's position offsets the diaphragm on the right, tenting it upward, while the diaphragm on the left is unaffected. The lungs have two lobes on the left and three on the right. These and other asymmetries drive predictable positional imbalances throughout the body. Many of these are tied into respiration. As a result, not only does the spine rotate in a predictable and injurious fashion, people tend to baseline in spinal extension, which induces a state of chronic sympathetic tone, reduced ANS variability and a host of physiological issues, partially due to activation of sympathetic spinal ganglia. This has profound impacts on everything from physical performance to sleep quality and stress management. A combination of these asymmetries, the postural influences and chronic, mild stress-state of modern life and other factors produce predictable and measurable changes in breathing, spinal and rib positioning and autonomic function. Being able to monitor and adjust these factors dynamically during training based on near real-time feedback is immensely valuable, and is where garment system 50 may be uniquely capable.

Garment system 50 may allow for monitoring of the asymmetric, multi-planar (transverse, sagittal and frontal) movement of the abdomen, spine and thorax during respiration and movement. Garment system 50 may also provide a direct window into cardiac workload and autonomic balance via heart rate and heart rate variability monitoring. This provides a valuable form of training feedback for everything from intense military training scenarios to strength and endurance training to meditative biofeedback exercises.

By utilizing embodiments of garment system 50 with one or more sub-systems described herein, the garment system may recognize the position of certain body parts that may correlate with a specific posture of an individual's body. For example, garment system 50 may categorize an individual's spinal position as found in either FIG. 15 or FIG. 16. This categorization may be determined by running a current through a plurality of RMSs 116 and measuring the time lapsed from one sensor to another. This time measurement may be compared with other time measurements (via a processor) recorded from other garment systems 50 utilized by other individuals with varying spinal positions. Information may further be supplied about how an individual may alter their spinal position if desired via the information gathered on other individual's varying spinal positions. Body parts that may be analyzed may include, but are not limited to the chest, the spine, and the pelvis.

Figure 17:
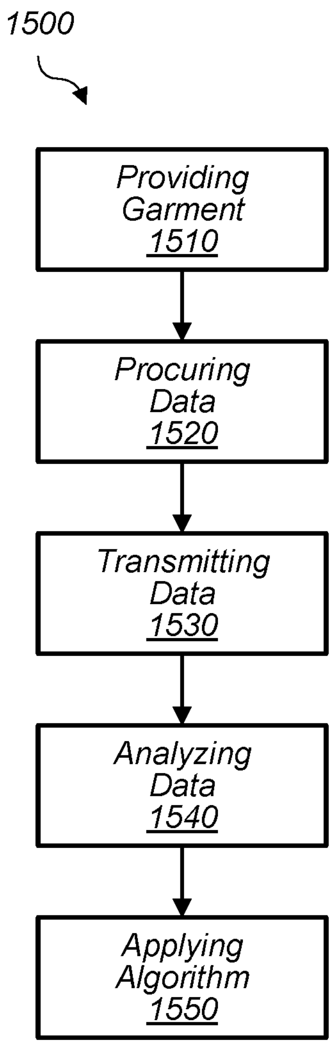
FIG. 17 displays an alternative embodiment of a method for collecting data.

FIG. 17 displays an alternative embodiment of method 1500 for collecting data. Method 1500 may utilize any embodiment of garment system 50 described herein. Method 1500 may include providing garment system 50 to an individual in 1510. Data may be procured in 1520 via at least one of processors 114 of garment system 50, respiratory monitor sub-system 110, GPS monitor 134, and/or at least one of the plurality of accelerometers 130. The procured data may then be transmitted in 1530 to at least one of processor 114 and the data analysis module. The procured data may be analyzed in 1540 via at least one of the processor 114 and the data analysis module. An algorithm may then be applied in 1550 to the procured data via at least one of processor 114 and the data analysis module in order to provide a processed output. The processed output may include biometric information associated with an individual wearing garment system 50.

Figure 18:
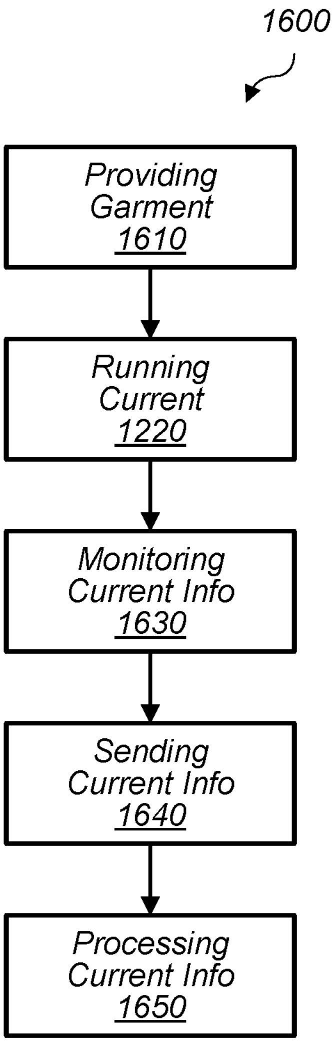
FIG. 18 displays an embodiment of a method for monitoring breathing.

FIG. 18 displays an embodiment of method 1600 for monitoring breathing. Method 1600 may utilize any embodiment of garment system 50 described herein. Method 1600 may include providing garment system 50 to an individual in 1610. Method 1600 may include running a current through at least some of the conductive flexible fibers and respiratory monitoring sites 116 in 1620. In certain embodiments, at least some of the conductive flexible fibers are in a nonlinear position in response to an applied force. In 1630, current information from respiratory monitoring sites 116 may be monitored and recorded. In some embodiments, the current information may include assigning a time stamp to the current at the point in time the current is received by respiratory monitoring sites 116. In 1640, the current information may be sent, via at least one of a wired network and a wireless network, to processor 114. In some embodiments, the processor may utilize an algorithm to process the data. In 1650, the current information may be processed, via the algorithm, provide a processed output.

As described herein, garment system 50 may be used to assess (e.g., track) various biometric properties including, but not limited to, body position, body motion, and vital signs (e.g., heart rate and respiration rate). Assessment of biometric properties using garment system 50 may be useful for many different implementations of the garment system. For example, the garment system may be used to track the various biometric properties during physical exertion events (e.g., exercise or stress events) and/or to track the various biometric properties for medical assessments (e.g., track biometrics for medical patients or during clinical studies). In certain embodiments, signals (e.g., either wired or wireless signals) associated with the various biometric properties that are received at processor 114 are synchronized to be on the same clock. For example, the signals may be synchronized to be on the same system clock (such as the clock for processor 114).

Figure 19:
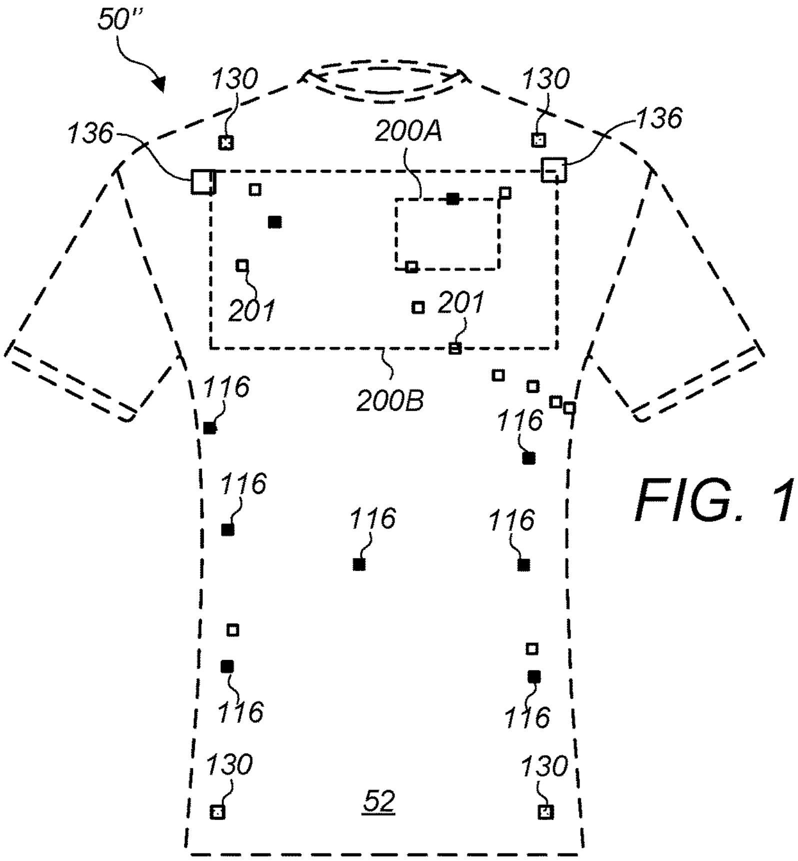
FIG. 19 depicts an anterior view representation of another embodiment of a garment system.
Figure 21:
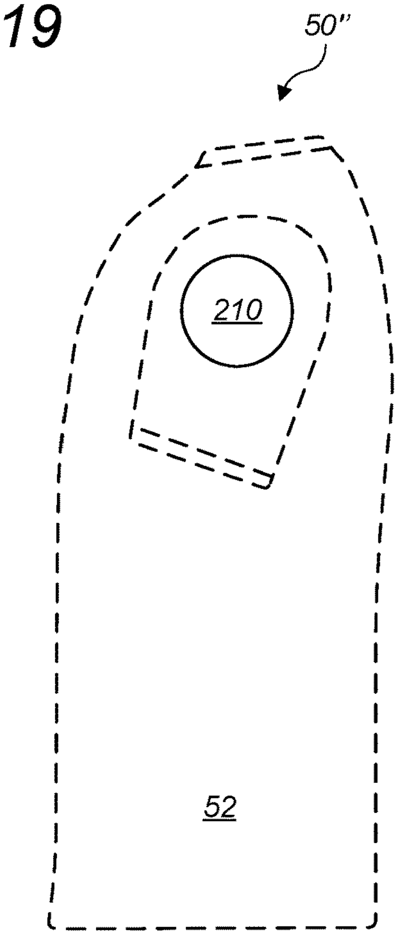
FIG. 21 depicts a side view representation of another embodiment of a garment system.
Figure 20:
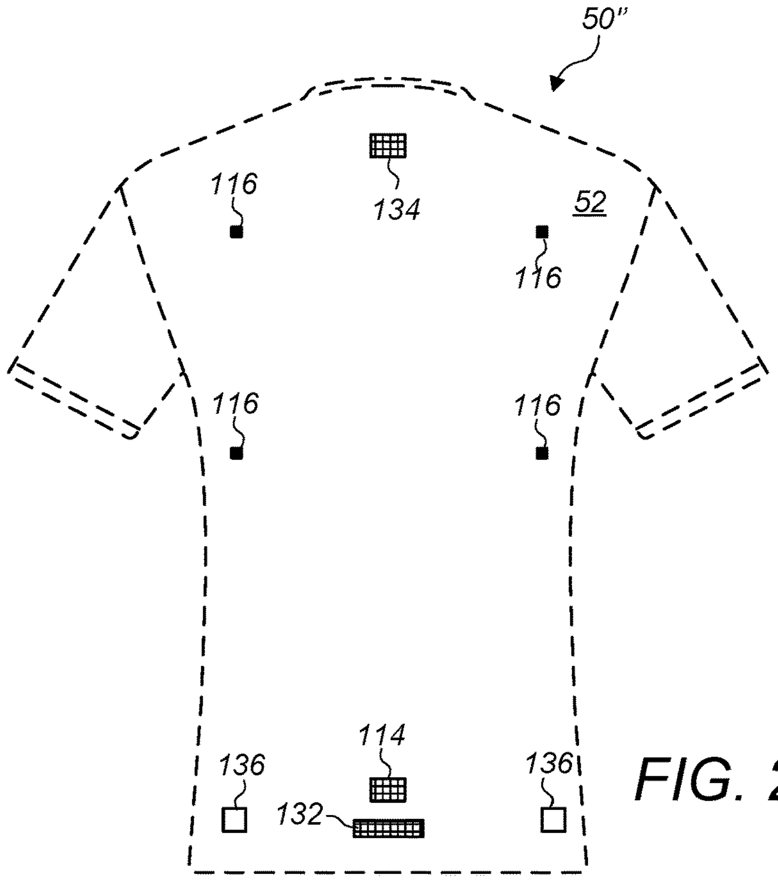
FIG. 20 depicts a posterior view representation of another embodiment of a garment system.

FIG. 19 depicts an anterior view representation of another embodiment of garment system 50". FIG. 20 depicts a posterior view representation of the embodiment of garment system 50". FIG. 21 depicts a side view representation of the embodiment of garment system 50". Garment system 50" may be used to assess biometric properties of a wearer of the garment system. In some embodiments, garment system 50" is capable of providing additional capabilities for the detection and/or treatment of medical conditions using the garment system. It is to be understood that components of garment system 50" are interchangeable with components of other garment systems described herein (e.g., garment system 50). It should also be understood that garment system 50" may be used in embodiments intended for use in the detection and/or treatment of medical conditions and/or in embodiments intended solely for the assessment of biometric properties. In certain embodiments intended solely for the assessment of biometric properties, components intended for use in detection and/or treatment of medical conditions may be removed from garment system 50".

In certain embodiments, as shown in FIG. 19, garment system 50" includes EKG (electrocardiography) sensors 201. EKG sensors 201 may be generally located at positions accepted for monitoring EKG via traditional methods. EKG sensors 201 may be used to provide real-time EKG monitoring. EKG monitoring may provide the ability to measure HRR, HRV, and hemodynamic waveforms.

In certain embodiments, as shown in FIG. 19, garment system 50" includes one or more environmental sensors 200 integrated in garment body 52. Sensor 200 may be integrated into a fabric used for garment body 52. In certain embodiments, sensor 200 is integrated in a layer of fabric that is exposed to an ambient environment surround garment body 52 (e.g., the sensors are in contact with the air around the garment body). For example, sensor 200 may be a panel in the outer layer of garment body 52.

The size of sensor 200 may be varied depending on a desired design for garment body 52. For example, as shown in FIG. 19, sensor 200 may be sensor 200A or sensor 200B. Sensor 200A may be used for smaller designs of garment body 52 (e.g., for use with small children) while sensor 200B may be used for larger designs of garment body 52 (e.g., for larger children and/or adults). The size of sensor 200 may also vary based on desired indicator requirements (e.g., color indication described below) and/or a sensitivity requirement of the sensor for a certain chemical (e.g., a sensor may need a minimum size to provide suitable environmental detection sensitivity).

Sensor 200 may be used to assess one or more environmental conditions in the ambient environment surrounding garment body 52. In certain embodiments, assessing environmental conditions includes assessing or monitoring for particulate matter in the ambient environment surrounding garment body 52 (e.g., assessing exposure of garment body 52 to particulate matter). In some embodiments, assessing or monitoring for particulate matter includes sensing (or detecting) the presence of particulate matter and/or assessing the concentration of the particulate matter in the ambient environment surrounding garment body 52. Particulate matter assessed by sensor 200 may include particulates in solid, liquid, and/or gaseous form. In some embodiments, particulate matter assessed by sensor 200 includes aerosolized matter. Particulate matter that may be assessed by sensor 200 includes, but is not limited to, food allergens (e.g., peanuts, soy, tree nuts, etc.), chemicals (can be aerosolized, solid, or liquid), radiation (or any other energy emission of interest), environmental allergens (e.g., airborne allergens).

In certain embodiments, sensor 200 provides assessment or monitoring of a specific particulate matter. For example, sensor 200 may provide assessment or monitoring for a specific allergen to which a wearer of garment body 52 is highly allergic. In some embodiments, sensor 200 provides assessment or monitoring of multiple particulate matters (e.g., a combination of particulate matters). For example, in a laboratory environment, sensor 200 may be capable of assessing or monitoring for a combination of radiation and hazardous chemicals.

In certain embodiments, sensor 200 provides visual indication of the presence and/or concentration of particulate matter in the ambient environment surrounding garment body 52 (e.g., when the sensor is exposed to particulate matter). For example, sensor 200 may include a chromatic (color changing) indicator that changes colors when the sensor is exposed to selected particulate matter (e.g., selected allergens or chemicals). In certain embodiments, sensor 200 is a panel that changes colors when the panel is exposed to a selected particulate matter. In some embodiments, sensor 200 is a chemochromatic panel that changes colors when the panel is exposed to a selected chemical.

Sensor 200 may turn a selected color when the sensor is exposed to a selected particulate matter. For example, sensor 200 may turn red (or bright red) when exposed to a selected allergen or a selected hazardous chemical. Red may be used to indicate exposure as red is generally recognized as a warning signal color. In certain embodiments, sensor 200 returns to its original (base) color if the sensor is no longer exposed to the selected particulate matter (e.g., when the allergen or hazardous chemical is no longer present in the ambient environment surrounding garment body 52).

In certain embodiments, sensor 200 provides output data associated with the assessment of particulate matter in the ambient environment surround garment body 52. Processor 114 (or another processor associated with garment system 50) may be coupled to sensor 200 (e.g., either wired or wirelessly coupled) and receive output data from the sensor). For example, sensor 200 may output "false" or "true" signals based on a status of detection of particulate matter where the "false" signal indicates there is no exposure to particulate matter of interest (e.g., the selected particulate matter) and the "true" signal indicates there is exposure to particulate matter of interest. Processor 114 may receive the outputs and assess beginning and/or ending of exposure to particulate matter based on the sequence of false/true signals. In some embodiments, the false/true signals are associated with indicator (e.g., color) changes in sensor 200. For example, the false signal may be associated with no color change (e.g., base color) where the true signal is associated with the color change (e.g., turn red) in sensor 200.

In certain embodiments, processor 114 assesses data received from sensor 200 to assess a condition of the wearer (e.g., a medical condition of the wearer). Data received from sensor 200 may be combined with other data assessed by garment system 50" to assess the condition of the wearer. For example, data received from sensor 200 may be combined with vital sign data and/or body position data assessed by garment system 50" to assess the condition of the wearer. Assessing data from sensor 200 in combination with other data assessed by garment system 50" may provide instantaneous feedback that may be used to proactively assess the condition of the wearer of garment body 52. Garment system 50" may be capable of rapid assessment of changes in the condition of the wearer based on data from sensor 200 and other data such as vital signs, body position, and other physiological information. In certain embodiments, signals (e.g., either wired or wireless signals) received at processor 114 (including signals from sensor 200 and other vital sign and/or body position data) are synchronized to be on the same clock (e.g., the same system clock for processor 114).

In certain embodiments, processor 114 transmits data from sensor 200 (along with other data) to another device (e.g., a wireless radio enable device, a Wi-Fi device, or a Bluetooth device). Data received from processor 114 may be displayed on the device using an application on the device (as described herein). In certain embodiments, the application may display on the device data such as, but not limited to, real-time location of the wearer (e.g., via GPS data), vital sign data, data from sensor 200 (e.g., environmental data), and other physiological data. The application may also store data on the device so that the wearer's data history can be accessed. In some embodiments, the application may transmit data for storage on a remote server (e.g., a cloud-based server).

In some embodiments, processor 114 and/or the application receiving data from the processor provide communications that notify one or more entities of the assessed condition of wearer. For example, a medical entity or a responsible party for the wearer may receive communications providing the assessed condition of wearer. In some embodiments, processor 114 and/or the application receiving data from the processor provide the assessed condition of the wearer to the entities when the condition of the wearer is an alert condition. For example, when the wearer is assessed to be under duress or in a condition needing medical attention, as described herein.

In certain embodiments, as shown in FIG. 21, garment system 50" includes fluid delivery system 210. Fluid delivery system 210 may be used to provide fluid injection into the body of the wearer of garment body 52. Fluid delivery system 210 may be, for example, a drug delivery system to provide drug delivery into the body of the wearer (e.g., drug injection). In some embodiments, fluid delivery system 210 includes one or more components on garment body 52 that are removable and/or replaceable (e.g., the components can be removed and replaced after use). In some embodiments, fluid delivery system 210 is positioned under a patch or other emblem to cover and/or disguise the fluid delivery system. For example, fluid delivery system 210 may be positioned under a patch on the sleeve of garment body 52.

Figure 22:
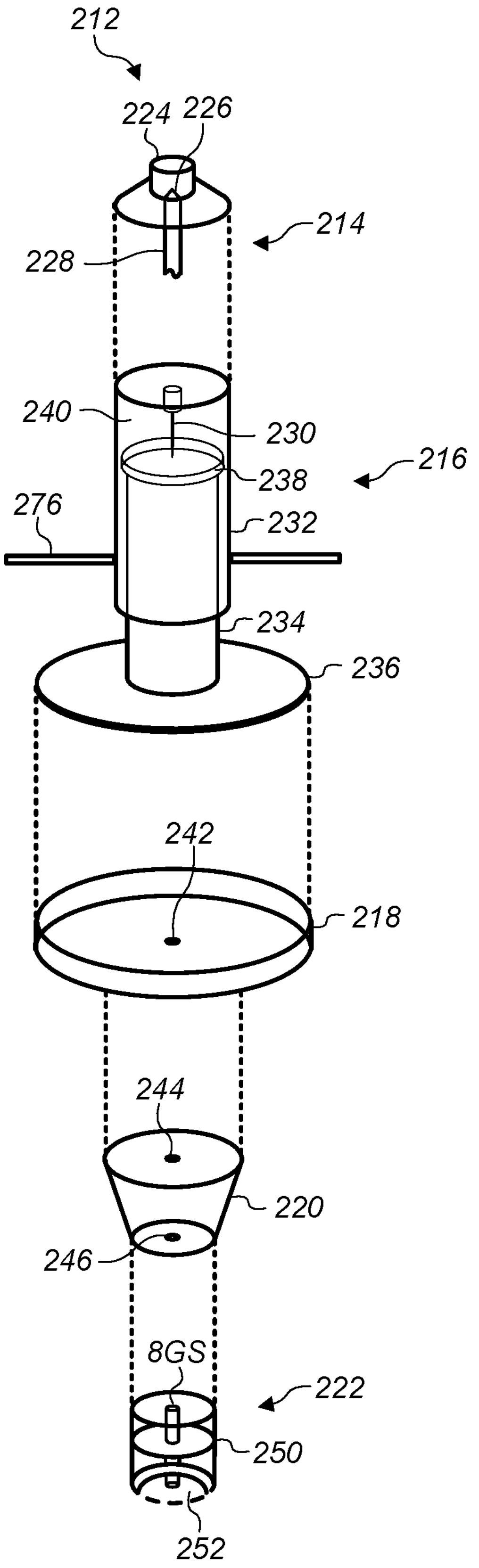
FIG. 22 depicts an exploded view representation of an embodiment of a fluid delivery system.

In certain embodiments, fluid delivery system 210 includes an injector assembly. FIG. 22 depicts an exploded view representation of an embodiment of injector assembly 212. In certain embodiments, injector assembly 212 includes trigger portion 214, piston portion 216, first chamber 218, second chamber 220, and injector portion 222. Trigger portion 214 may include safety cap 224, trigger 226, and pin 228. Safety cap 224 may be a hinged safety cap that, when closed, prevents accidental pushing of trigger 226. Trigger 226 may be coupled to pin 228 such that moving the trigger moves the pin. For example, trigger 226 may be a push button or other device that can be pushed to move pin 228 towards piston portion 216.

Piston portion 216 may include pin 230, piston cylinder 232, piston 234, and piston base 236. In some embodiments, pin 230 and pin 228 are separate pins that engage each other. In some embodiments, pin 230 and pin 228 are different portions of a single pin. A lower end of pin 230 may be shaped to puncture an upper surface of piston seat 238. In some embodiments, pin 230 is supported by a spring and the force applied to trigger 226 has to overcome the spring force to allow pin 230 to puncture the upper surface of piston seat 238.

Piston seat 238 may include a $CO_2$ or other pressurized gas cartridge. Puncturing of the surface of piston seat 238 may release the pressurized gas from the piston seat. In some embodiments, the edges of piston seat 238 are beveled. The beveled edges may provide a base for a gas/reaction chamber in space 240 (e.g., the space between piston seat 238 and piston cylinder 232). When pressurized gas is released in space 240, the increase in pressure in the space moves piston 234 and piston base 236 downwards towards first chamber 218.

Figure 23:
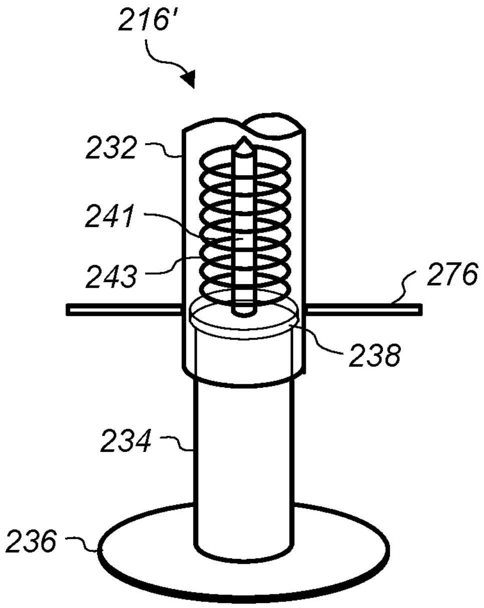
FIG. 23 depicts a representation of an alternative embodiment of a piston portion.

FIG. 23 depicts a representation of an alternative embodiment of piston portion 216'. Piston portion 216' may include post 241 and spring 243 inside piston cylinder 232. Spring 243 may provide force to move piston 234 and piston base 236 downwards towards first chamber 218 when trigger 226 is operated.

As shown in FIG. 22, piston 234 and piston base 236 may move downwards towards first chamber 218 when trigger 226 is operated. First chamber 218 may be, for example, a capsule or other container that contains fluids (e.g., drugs) intended for injection into the wearer's body. Piston base 236 may function as the upper surface or top of first chamber 218. Thus, when piston base 236 moves downwards, the piston base may move fluids out of first chamber 218 through output port 242 in the bottom of the first chamber. In certain embodiments, the bottom of piston base 236 is flat. The bottom of piston base 236 may, however, have other shapes (e.g., convex) depending on the needs for moving fluids out of first chamber 218.

In some embodiments, output port 242 is an opening with a semipermeable membrane covering the opening. The membrane may have a selected surface tension that is overcome by the pressure of piston base 236 moving fluids out of first chamber 218. In some embodiments, output port 242 includes a one-way valve that opens with the force generated by piston base 236 moving fluids out of first chamber 218.

As fluids move out of first chamber 218 through output port 242, the fluids may move into second chamber 220 through input port 244. Input port 244 may include an opening with a semipermeable membrane or a one-way valve similar to output port 242. In certain embodiments, the force needed to move fluids through input port 244 is less than the force needed to move fluids through output port 242. For example, the force needed to move fluids through input port 244 may be about 80% of the force needed to move fluids through output port 242.

Fluids may be moved out of second chamber 220 through output port 246. Output port 246 may include an opening with a semipermeable membrane or a one-way valve similar to output port 242 and input port 244. The force needed to move fluids through output port 246 may less than the force needed to move fluids through output port 242. For example, the force needed to move fluids through output port 246 may be about 10% of the force needed to move fluids through output port 242. In certain embodiments, second chamber 220 is cone shaped. The cone shape of second chamber 220 may increase the forces on the fluids as the fluids move out of the second chamber.

Fluids may be moved through output port 246 into injector portion 222. Injector portion 222 may include injection tube 248. In certain embodiments, injection tube 248 has a diameter of between about 0.03 mm and about 0.06 mm. The diameter of injection tube 248 may be selected to provide the ability to inject fluids through the skin of the wearer of garment body 52. Other diameters for injection tube 248 may also be contemplated depending on the type of fluids to be injected. In certain embodiments, injector portion 222 has floor 250 with recess 252 below the floor. Recess 252 may be on the bottom portion of the exterior of injector portion 222 that contacts the skin of the wearer. Recess 252 may be shaped (e.g., have concave walls) such that when injector portion 222 is pressed against the skin of the wearer, at least some skin fills into the recess. Skin filling recess 252 may provide increased likelihood of successful injection of fluid into the body of the wearer.

As shown in FIG. 22, when trigger 226 is pressed, injector assembly 212 operates to inject fluids (e.g., drugs) positioned in primary chamber 218 into the body of the wearer. When trigger 226 is pressed, fluids are forced into injection tube 248 by the downward force of piston base 236. Downward forces are also applied to injection tube 248. When activated, the forces at the end of injection tube 248 contacting the skin of the wearer may be sufficient to overcome the ultimate tensile strength (UTS) of dermal and subcutaneous tissue in the skin of the wearer (e.g., the force at the end of the injection tube is at least about 3200 psi). Overcoming the tensile strength of the tissue allows the fluids to be injected into the body of the wearer a sufficient depth for the fluids to enter the bloodstream.

In certain embodiments, injector assembly 212 is coupled to garment body 52 at the location of a port or other opening in the garment body (e.g., a port in the sleeve of the garment body). The port may allow contact between injector assembly 212 and the skin of the wearer of garment body 52. The port may be integrated in garment body 52. In some embodiments, the port includes a mechanism for coupling injector assembly 212 to garment body 52. The mechanism may also secure injector assembly 212 to garment body 52.

Figure 24:
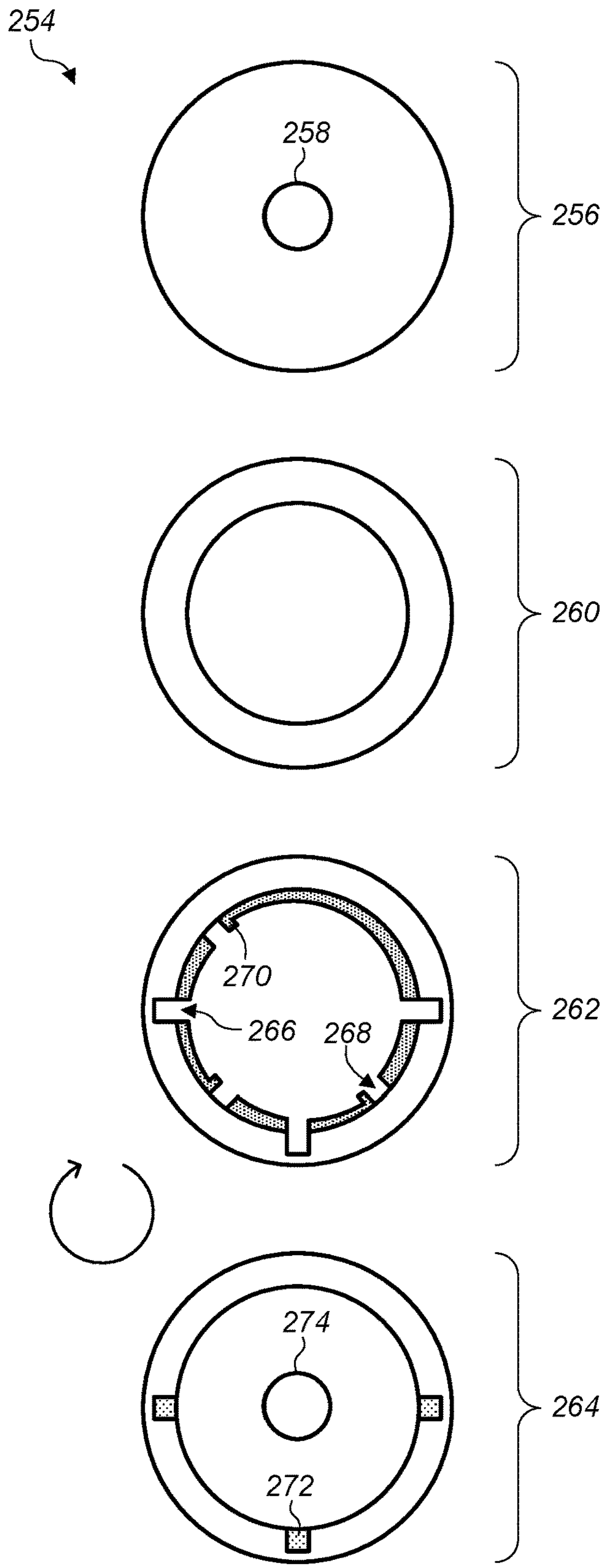
FIG. 24 depicts a representation of an embodiment of a port.

FIG. 24 depicts a representation of an embodiment of port 254. Port 254 may be integrated in garment body 52 to provide access to the skin of the wearer of the garment body for fluid delivery system 210. Port 254 may include base 256. In certain embodiments, base 256 is embedded in garment body 52 (e.g., embedded in the fabric of the garment body).

Base 256 may be made of semi-rigid, non-permeable material such as polycarbonate. Base 256 may include opening 258. Opening 258 may be sized to accommodate a nozzle or other injector for delivery of fluids beneath the skin of the wearer. For example, opening 258 may be sized to accommodate injection tube 248 of injector assembly 212. In some embodiments, opening 258 has a size between about 0.05 mm and about 0.20 mm, between about 0.07 mm and about 0.19 mm, or between about 0.09 mm and about 0.18 mm.

In certain embodiments, port 254 includes gasket 260, receiver 262, and lock 264. Gasket 260 may be, for example, a sponge gasket or similar material. Receiver 262 and lock 264 may be made of semi-rigid, or rigid, non-permeable materials such as polycarbonate. Receiver 262 may include keyholes 266, key seats 268, and key stops 270 distributed around the receiver. Lock 264 may include teeth 272 and opening 274. Opening 274 may be sized to accommodate a nozzle (e.g., injection tube 248) for delivery of fluids beneath the skin of the wearer.

In certain embodiments, receiver 262 is coupled to base 256 with gasket 260. Lock 264 may then operate with receiver 262 to couple injector assembly 212 to port 254. For example, lock 264 may be seated on receiver 262 and rotated in the direction of the arrow to engage teeth 272 with key seats 268 and secure the lock to the receiver. In some embodiments, injector assembly 212 may include arms 276 (shown in FIGS. 22 and 23) that interact with receiver 262 and lock 264 to secure the injector assembly to port 254. Securing injector assembly 212 to port 254 attaches the injector assembly to garment body 52.

As described above, injector assembly 212 may be used in fluid delivery system 210 to inject fluids (e.g., drugs) into the wearer of garment body 52. In certain embodiments, injector assembly 212 is a single use injector (e.g., the injector assembly is disposable). After fluids are injected into the wearer from injector assembly 212, the injector assembly may be removed from garment body 52 (e.g., decoupled from port 254) and then discarded or recycled. In some embodiments, a new injector assembly is coupled to garment body 52 (e.g., coupled to port 254) after a used injector assembly is removed. Thus, garment body 52 may be reused for multiple injection assemblies as needed by the wearer of the garment body.

In certain embodiments, activation of injector assembly 212 is controlled by processor 114 (or another processor associated with garment system 50). Processor 114 may control activation of injector assembly 212 based on the assessed condition of the wearer of garment body 52 (e.g., the assessed medical condition of the wearer). As described herein, assessing the condition of the wearer may include assessing vital signs and/or body position of the wearer using garment system 50 along with assessing ambient environmental conditions using sensor 200. Processor 114 may assess the combination of vital signs, body position, and/or ambient environmental conditions to determine if the wearer is in a condition or state (e.g., a medical condition or state) that necessitates the injection of fluids (e.g., drugs) from injector assembly 212 into the wearer's body. For example, processor 114 may determine if the wearer is simply in an excited state (e.g., due to exercise), where injection of fluids is not needed, or the wearer is in a medical emergency state (e.g., due to an allergic reaction), where the injection of drugs (e.g., epinephrine) may be life-saving.

In some embodiments, processor 114 controls activation of injector assembly 212 by controlling access to trigger 226. For example, safety cap 224 may be prevented from being opened to access trigger 226 by an electronic latch or lock unless processor 114 detects that the assessed condition of the wearer necessitates the injection of fluids from injector assembly 212. Controlling access to the activation mechanism (e.g., trigger 226) of injector assembly 212 may prevent the injection of fluids (e.g., drugs) into the wearer's body in non-necessary circumstances (e.g., when the wearer is simply in an excited state due to exercise).

Figure 25:
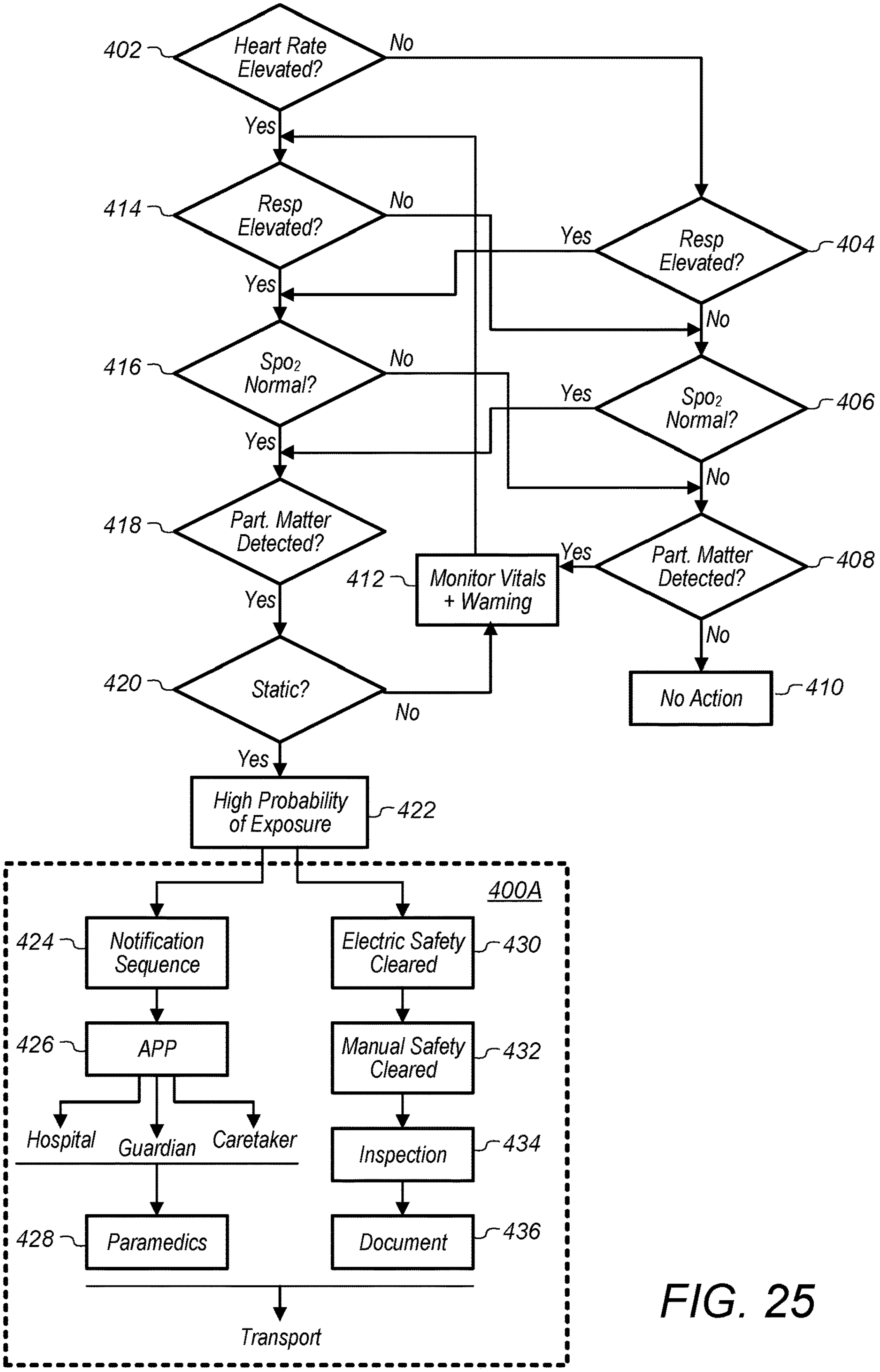
FIG. 25 depicts a flowchart of an embodiment of a control method using a garment system.

FIG. 25 depicts a flowchart of an embodiment of control method 400 using garment system 50. Method 400 may be used to assess the condition (e.g., medical condition) of the wearer to determine if the wearer needs medical attention and/or if injector assembly 212 should be allowed to be used for injection of fluids into the wearer's body. In certain embodiments, method 400 is implemented by processor 114 (or another processor associated with garment system 50).

In 402, garment system 50 detects if the heart rate of the wearer of garment body 52 is elevated. For example, a heart rate monitor integrated in garment body 52 may be used to assess the heart rate of the wearer. If the heart rate is not elevated, method 400 continues with determining if respiration is elevated in 404. If respiration is not elevated, then SpO2 levels are assessed to see if they in a normal range in 406. If SpO2 levels are not normal (e.g., are below normal levels), then presence of selected particulate matter (e.g., allergen) is assessed in 408 (e.g., assess color change in sensor 200). If no selected particulate matter is detected, then the condition of the wearer is determined to be normal and no further action is taken in 410. If selected particulate matter is detected in 408 (but without any elevated vital signs), then a monitor vital signs signal and warning may be provided in 412 and respiration and SpO2 may continue to be monitored in 414 and 416. Monitoring of respiration and SpO2 may be monitored after detection of selected particulate matter due to the possibility of a delayed reaction to the particulate matter.

If respiration is determined to be elevated in 404 after a non-elevated heart rate is determined, this may indicate that the wearer is in a potentially heightened condition. In such cases, both SpO2 level (in 416) and selected particulate matter detection (in 418) may need to be determined in addition to the respiration level to assess the condition of the wearer. Similarly, if SpO2 level is determined to be below normal in 406 after a non-elevated respiration level is determined in 404, this may indicate that the wearer is in a potentially heightened condition. In this case, selected particulate matter detection (in 418) may need to be determined to assess the condition of the wearer. It is to be understood that while the embodiment of method 400 described above is described with a logical flow (e.g., 402 then 404 then 406), the logical flow of method 400 may vary as allowable. For example, the logical flow may include 404 then 402 then 406 or any other logical flow that is reasonably to apply to method 400.

As shown by the process flow in FIG. 25, if the detection of selected particulate matter in 418 is positive ("Yes") along with a combination of one more the other factors of elevated heart rate, elevated respiration, or low SpO2 levels, then the body position or motion of the wearer may be assessed in 420. If the wearer is detected to be static (e.g., no motion or movement of the body), then a high probability of exposure is assessed in 422 and method 400 may proceed with a treatment protocol in box 400A. If the wearer is detected to be moving (e.g., not static), then method 400 may cycle back to the monitor vital signs signal and warning provided in 412. In some embodiments, assessing body position in 420 may include assessing a posture of the wearer. For example, is the wearer hunched over, standing upright, sitting, etc.

In certain embodiments, processor 114 outputs a signal providing an indication of the assessed condition of the wearer. The signal may be, for example, a visual signal and/or a signal provided to the application associated with garment system 50. The signal may indicate a level of the assessed condition of the wearer. For example, is the wearer in a warning state (such as provided in 412 above), in an alert state (where the wearer is a more alarmed condition), or an emergency state (where medical attention is likely needed). In some embodiments, the signal provided is based on the number of biometric measurements that are determined to be in stressed states in combination with environmental detection by sensor 200.

Figure 26:
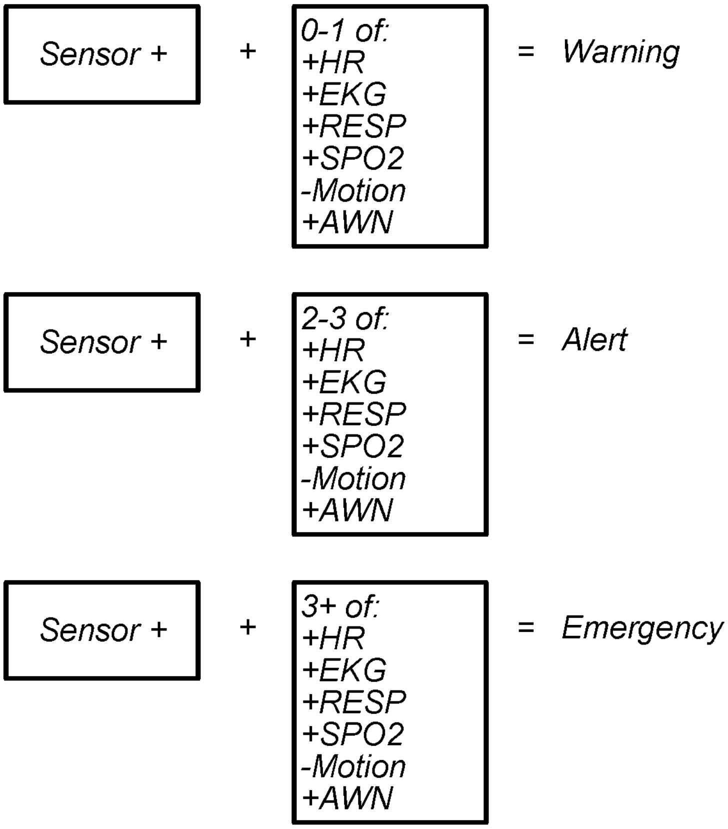
FIG. 26 depicts a representation of an embodiment of conditions needed for different signal levels.

FIG. 26 depicts a representation of an embodiment of conditions needed for different signal levels. For the "Warning" level, sensor 200 detects the selected particulate matter ("Sensor+") in combination with 0-1 of the selected biometric measurements indicating possible stressed states for the wearer. The selected biometric measurements may be "+HR" (elevated heart rate), "+EKG" (raised EKG monitoring), "+RESP" (elevated respiration rate), "+SPO2" (low SPO2 level), "−Motion" (static or little motion of wearer), and "+AWN". The "Warning" level may indicate that the wearer's vital signs/biometrics are acceptable, but he/she should be monitored for potential changes in condition.

The "Alert" level may be a raised level from the "Warning" level. For the "Alert" level, sensor 200 detects the selected particulate matter in combination with 2-3 of the selected biometric measurements. At the "Alert" level, the condition of the wearer needs to be more closely monitored as the condition could change rapidly. For the "Emergency" level, sensor 200 detects the selected particulate matter in combination with 3 or more of the selected biometric measurements. At the "Emergency" level, the wearer needs medical attention and garment system 50 may start providing notification and following protocol to provide treatment for the wearer.

In certain embodiments, the treatment protocol in box 400A, shown in FIG. 25, includes providing notification of the condition of the wearer and operating steps for the activation and use of injection assembly 212 to inject fluids into the wearer's body. Notification sequence 424 may include, for example, providing an output indicative of the assessed condition (e.g., the assessed medical alert condition) of the wearer. In certain embodiments, notification sequence 424 includes, in 426, providing information (e.g., an urgent condition notification) to an application associated with garment system 50 (e.g., an app on a mobile device connected to processor 114). The application may provide the notification of the urgent condition of the wearer to one or more entities. For example, the notification may be provided to a hospital, a guardian, or another caretaker. In 428, notification along with medical information for the wearer may be provided to emergency personnel (e.g., paramedics or EMTs) that may then transport the patient to a medical facility or other location.

The operating steps for activation and use of injection assembly 212 may include releasing an electric safety for the injection assembly in 430. Releasing the electric safety may include processor 114 removing the electronic lock or latch that prevents opening of safety cap 224. In 432, safety cap 224 may be manually opened to access trigger 226. In 434, injection of fluids may be provided by operating trigger 226. In 436, the injection may be documented. Documentation of the injection may also be provided to the notification sequence so that the entities are aware that the injection has taken place.

The following non-limiting examples are provided for different scenarios in which processor 114 assesses the condition of the wearer and the processor allows or prevents access to activation of injector assembly 212.

First Example Scenario

The wearer of garment system 50 is an 11-year old boy with a known bee allergy. The boy is playing (e.g., at recess at school). Garment system 50 detects that the boy has a respiration rate of 35 and sinus tachycardia with a heart rate of 175 bpm. SpO2 saturation is at 94% with a decrease of 6% from the baseline in the last three minutes. The GPS monitor indicates movement on a school playground and sensor 200 (e.g., the chemochromatic sensor) is reading false (e.g., no detection of selected particulate matter). Motion sensors on garment body 52 indicate that the boy is running with sudden stops, punctuated by intermittent throwing motions. Garment system 50 assesses these inputs to determine with a high degree of certainty that the changes in physiological output for the boy are likely due to exercise. Thus, no alert is sent by garment system 50.

Second Example Scenario

The wearer of garment system 50 is an 8-year old girl with a known food allergy. The girl is sitting in class during snack time. Garment system 50 detects that the girl has a respiration rate of 32 that has increase over 70% from her typical baseline. The cardiac monitor shows sinus tachycardia with a rate of 145 bpm, which shows an increase from a baseline of 75 bpm in the last 5 minutes. SpO2 saturation is 92% and falling. The GPS monitor shows the girl is not moving and is inside of her school. Processor 114 may assess that there is a high likelihood that the girl is in snack time in her classroom. Sensor 200 is reading true indicating that the girl has been exposed to the selected particulate matter (e.g., the food allergen). Motion sensors on garment body 52 indicate that the girl is in a static position and she has a hunched posture.

Garment system 50 assesses these inputs to determine with a high degree of certainty that the vital signs indicate physical stress associated with the onset of anaphylaxis. An alert may be sent by processor 114 (e.g., through a mobile application connected to the processor) to a predetermined set of entities including the parents or other guardians. Processor 114 may also notify a preferred local health facility (e.g., emergency room) and an emergency dispatch for an ambulance. Medical information about the condition of the girl may be provided along with the notifications. At the health facility, a physician (e.g., an on-call physician) may review the biometric data, generate a differential diagnosis for suspected anaphylaxis, and prepare for the girl's arrival.

At the same time, an adult (e.g., a teach or supervisor) in the classroom with knowledge of the girl's allergy may notice something is wrong and sensor 200 may provide visual indication that the girl has been exposed to the food allergen. Processor 114 may release the electronic latch or lock on injector assembly 200 and allow the adult to operate the injector assembly to administer the drug (e.g., epinephrine) into the girl's body. The health facility, the parents, and the arriving emergency transport personnel (e.g., paramedics) are alerted that the girl has been injected with the drug. At arrival, the paramedics may continue to monitor with traditional equipment and chart the girl and the injection of the drug as they prepare for and conduct transport to the health facility.

Figure 27:
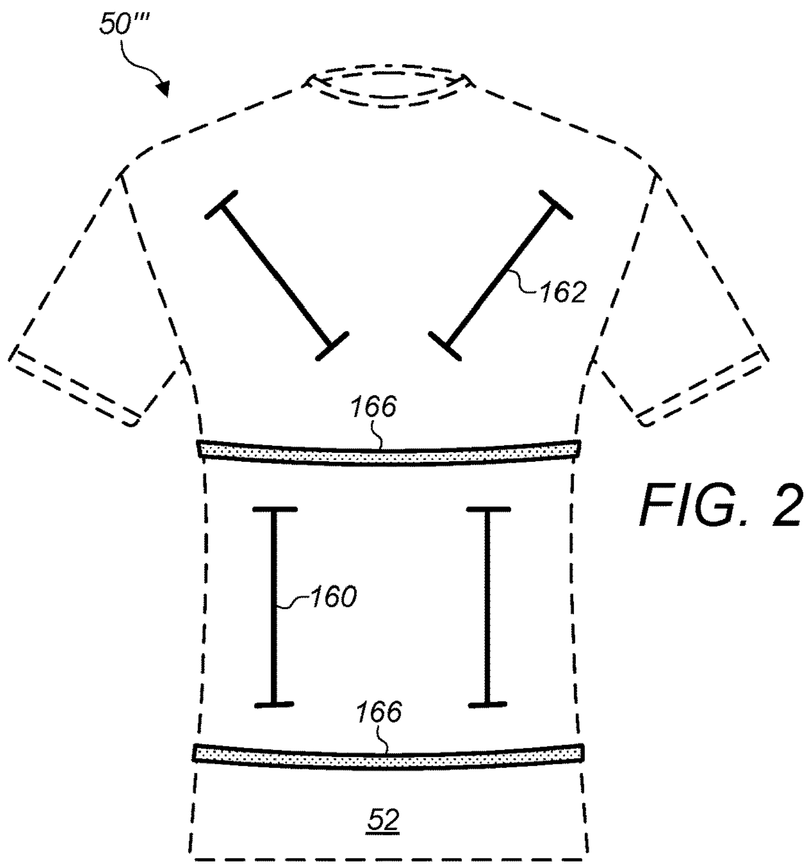
FIG. 27 depicts an anterior view representation of yet another embodiment of a garment system.
Figure 29:
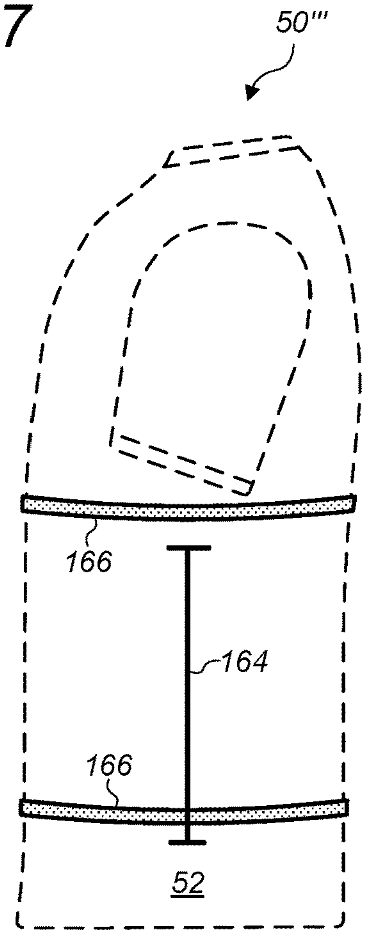
FIG. 29 depicts a side view representation of yet another embodiment of a garment system.
Figure 28:
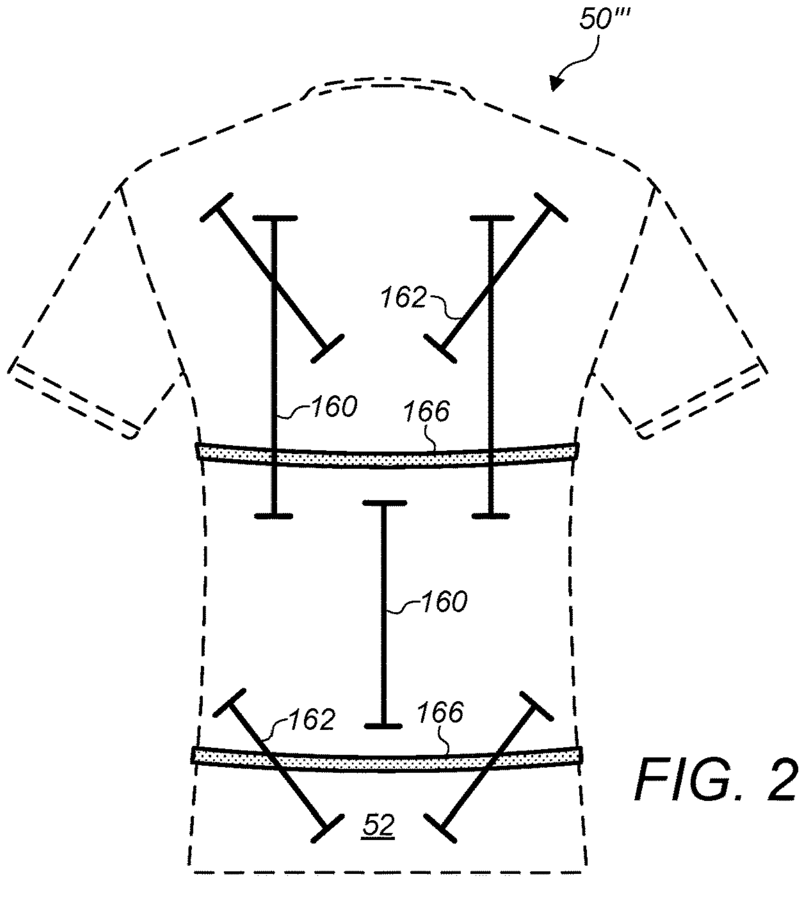
FIG. 28 depicts a posterior view representation of yet another embodiment of a garment system.

FIGS. 27-29 depict an embodiment of garment system 50'''. Garment system 50''' may be used to assess biometric properties of a wearer of the garment system. The embodiment of garment system 50''' depicted in FIGS. 27-29 is shown to include conductive elastic material (e.g., strands or fibers of a conductive elastomer) in garment body 52. It is to be understood that garment system 50''' may include other components of garment systems depicted herein (e.g., garment systems 50, 50', or 50'') and that the components of garment system 50''' are interchangeable with components of the other garment systems described herein. It should also be understood that garment system 50''' may be used in embodiments intended for use in the detection and/or treatment of medical conditions and/or in embodiments intended solely for the assessment of biometric properties.

FIG. 27 depicts an anterior view representation of the embodiment of garment system 50'''. FIG. 28 depicts a posterior view representation of the embodiment of garment system 50'''. In certain embodiments, the anterior and posterior sides of garment body 52 include vertical strips 160. Vertical strips 160 may be, for example, strips of conductive elastic material. The anterior and posterior sides of garment body 52 may also include transverse strips 162. Transverse strips 162 may be, for example, at an approximately 45° angle. Transverse strips 162 may also include strips of conductive elastic material in garment body 52.

In certain embodiments, vertical strips 160 are used to assess (e.g., measure) sagittal plane flexion and/or extension of the wearer of garment body 52. Transverse strips 162 may be used to assess (e.g., measure) asymmetrical expansion and/or rotation of the wearer of garment body 52. Vertical strips 160 and transverse strips 162 may measure these properties using techniques described herein for conductive elastic materials (e.g., assessment of resistance and/or strain in the materials).

FIG. 29 depicts a side view representation of the embodiment of garment system 50'''. In certain embodiments, the lateral sides of garment body 52 include vertical strips 164 (with a second strip being on the opposite side of the garment body shown in FIG. 29). Vertical strips 164 may include strips of conductive elastic material in garment body 52. In certain embodiments, vertical strips 164 are used to assess (e.g., measure) lateral flexion and/or extension of the wearer of garment body 52.

In certain embodiments, as shown in FIGS. 27-29, garment body 52 includes bands 166. Bands 166 may be, for example, barrel bands that encompass the circumference of garment body 52 (e.g., the bands cover the circumference of the body of the wearer of the garment body). Bands 166 may include conductive elastic material in garment body 52. In certain embodiments, bands 166 are used to assess (e.g., measure) expansion of the body wall of the wearer of garment body 52.

In certain embodiments, vertical strips 160, transverse strips 162, vertical strips 164, and/or bands 166 are connected to monitoring sites 116. For example, monitoring sites may be located at each end of the strips or at one or more locations along the bands. Monitoring sites 116 may be used to receive and/or transmit data from the strips and bands (e.g., transmit to and/or receive from a processor on garment body 52).

The combination of measurements from vertical strips 160, transverse strips 162, vertical strips 164, and bands 166 may be used to determine a three-dimensional image of motion of the wearer of garment body 52. The three-dimensional motion image may be combined with other measurement to provide an overall biometric assessment of the wearer of garment body 52. For example, the overall biometric assessment may include assessment of motion, body position, physical movement, and/or vital signs of the wearer.

Figure 30:
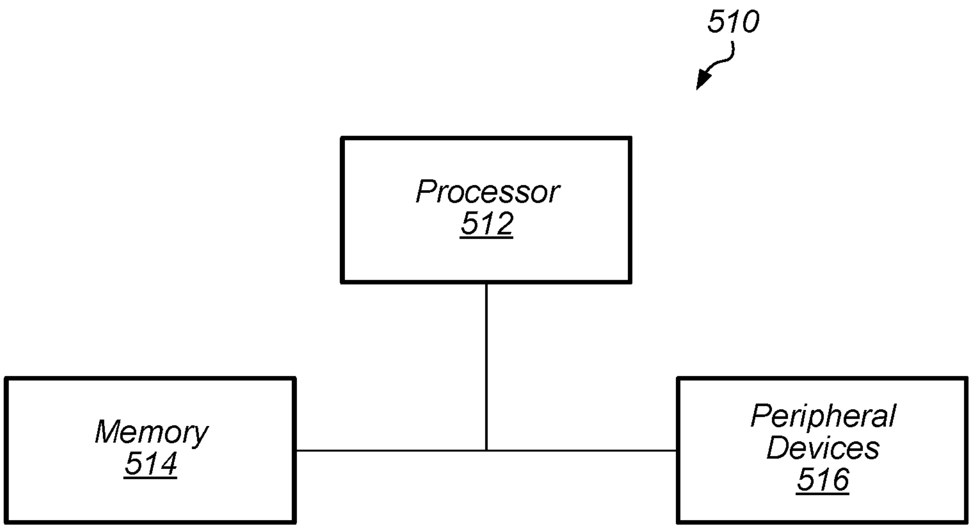
FIG. 30 depicts a block diagram of one embodiment of an exemplary computer system.

FIG. 30 depicts a block diagram of one embodiment of exemplary computer system 510. Exemplary computer system 510 may be used to implement one or more embodiments described herein. In some embodiments, computer system 510 is operable by a user to implement one or more embodiments described herein such as communication between processor 114 and a mobile device. In the embodiment of FIG. 30, computer system 510 includes processor 512, memory 514, and various peripheral devices 516. Processor 512 is coupled to memory 514 and peripheral devices 516. Processor 512 is configured to execute instructions, including the instructions for communication between garment system 50 and a mobile device, which may be in software. In various embodiments, processor 512 may implement any desired instruction set (e.g. Intel Architecture-32 (IA-32, also known as x86), IA-32 with 64-bit extensions, x86-64, PowerPC, Sparc, MIPS, ARM, IA-64, etc.). In some embodiments, computer system 510 may include more than one processor. Moreover, processor 512 may include one or more processors or one or more processor cores.

Processor 512 may be coupled to memory 514 and peripheral devices 516 in any desired fashion. For example, in some embodiments, processor 512 may be coupled to memory 514 and/or peripheral devices 516 via various interconnect. Alternatively or in addition, one or more bridge chips may be used to coupled processor 512, memory 514, and peripheral devices 516.

Memory 514 may comprise any type of memory system. For example, memory 514 may comprise DRAM, and more particularly double data rate (DDR) SDRAM, RDRAM, etc. A memory controller may be included to interface to memory 514, and/or processor 512 may include a memory controller. Memory 514 may store the instructions to be executed by processor 512 during use, data to be operated upon by the processor during use, etc.

Figure 31:
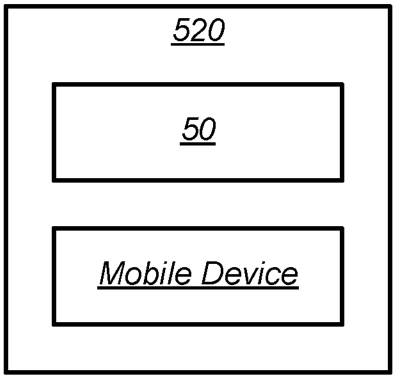
FIG. 31 depicts a block diagram of one embodiment of a computer accessible storage medium.

Peripheral devices 516 may represent any sort of hardware devices that may be included in computer system 510 or coupled thereto (e.g., storage devices, optionally including computer accessible storage medium 520, shown in FIG. 31, other input/output (I/O) devices such as video hardware, audio hardware, user interface devices, networking hardware, etc.).

Turning now to FIG. 31, a block diagram of one embodiment of computer accessible storage medium 520 including one or more data structures representative of garment system 50 included in an integrated circuit design and one or more code sequences representative of communication between garment system 50 and a mobile device. Each code sequence may include one or more instructions, which when executed by a processor in a computer, implement the operations described for the corresponding code sequence. Generally speaking, a computer accessible storage medium may include any storage media accessible by a computer during use to provide instructions and/or data to the computer. For example, a computer accessible storage medium may include non-transitory storage media such as magnetic or optical media, e.g., disk (fixed or removable), tape, CD-ROM, DVD-ROM, CD-R, CD-RW, DVD-R, DVD-RW, or Blu-Ray. Storage media may further include volatile or non-volatile memory media such as RAM (e.g. synchronous dynamic RAM (SDRAM), Rambus DRAM (RDRAM), static RAM (SRAM), etc.), ROM, or Flash memory. The storage media may be physically included within the computer to which the storage media provides instructions/data. Alternatively, the storage media may be connected to the computer. For example, the storage media may be connected to the computer over a network or wireless link, such as network attached storage. The storage media may be connected through a peripheral interface such as the Universal Serial Bus (USB). Generally, computer accessible storage medium 500 may store data in a non-transitory manner, where non-transitory in this context may refer to not transmitting the instructions/data on a signal. For example, non-transitory storage may be volatile (and may lose the stored instructions/data in response to a power down) or non-volatile.

Embodiments of the present disclosure may be realized in any of various forms. For example, some embodiments may be realized as a computer-implemented method, a computer-readable memory medium, or a computer system. Other embodiments may be realized using one or more custom-designed hardware devices such as ASICs. Other embodiments may be realized using one or more programmable hardware elements such as FPGAs (field programmable gate arrays).

In some embodiments, a non-transitory computer-readable memory medium may be configured so that it stores program instructions and/or data, where the program instructions, if executed by a computer system, cause the computer system to perform a method, e.g., any method embodiments described herein, or, any combination of the method embodiments described herein, or, any subset of any of the method embodiments described herein, or, any combination of such subsets.

In some embodiments, a wireless device (or wireless station) may be configured to include a processor (or a set of processors) and a memory medium, where the memory medium stores program instructions, where the processor is configured to read and execute the program instructions from the memory medium, where the program instructions are executable to cause the wireless device to implement any of the various method embodiments described herein (or, any combination of the method embodiments described herein, or, any subset of any of the method embodiments described herein, or, any combination of such subsets). The device may be realized in any of various forms.

In embodiments described herein, operating systems utilized by any part of garment system 50 may include, but not be limited to: iOS operating systems, Windows Phone operating systems, Windows operating systems, Android operating systems, BlackBerry operating systems, Linux systems, and Unison operating systems.

In embodiments described herein, any of the electronic components of garment system 50 may include a waterproof coating (e.g., a waterproof nanocoating) adhered to the exterior of the electronic components. The coating may allow for the components to function properly when garment system 50 is exposed to a wet environment that may include sweat and/or water.

In embodiments described herein, wiring connecting two or more electronic components found in garment system 50 may be contained within a multi-layered fabric construction. In some embodiments, the wiring may be partially engrained within seams in garment body 52. In some embodiments, the wiring may comprise conductive fibers. The conductive fibers may be in the form of one or more yarns woven or knit with other fibers. In some embodiments, the yarns may be coated with an insulative polymer to, for example, provide efficient transfer of power or data.

In embodiments described herein, garment system 50 may be capable of monitoring multiple biometric responses such as, but not limited to: skin temperature, core temperature, respirations, heart rate, predicted tidal volume, chest wall movement, abdominal movement in conjunction with inspiration, abdominal movement in conjunction with expiration, HRR (heart rate reserve), HRV (heart rate variability), body position relevant to perpendicular, shoulder position relevant to hip position, general body posture, up time, down time, and malfunctions.

In embodiments described herein, garment system 50 may be capable of monitoring multiple biometric peripheral processes through Bluetooth Smart or similar. These biometric peripheral processes may include, but not be limited to: DTR, eye movement, eye position, reflex velocity, visual tracking, visual focal points, tactile response, and skin conductivity.

In embodiments described herein, garment system 50 may be a garment other than a shirt. These other garments may include any of the structures and/or functionalities described herein. In some embodiments, fabric within garment body 50 may include a twill weave. The twill weave may provide a better form fitting structure to the body by allowing the garment body to succumb easier to flexing or folding to match the curves of a body.

As described herein, the term "garment" may refer to a belt in some embodiments. As described herein, the terms "garment", "garment system", and "system 50" may be synonymous. As described herein, the terms "respiration/skeletal position monitors", "RMSs", and "respiration monitoring sites" may be synonymous. As described herein, the terms "respiration monitor sub-system" and "respiration monitoring sub-system" may be synonymous. As described herein, the terms "battery unit" and "battery" may be synonymous.

Although specific embodiments have been described above, these embodiments are not intended to limit the scope of the present disclosure, even where only a single embodiment is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

Further modifications and alternative embodiments of various aspects of the embodiments described in this disclosure will be apparent to those skilled in the art in view of this description. Accordingly, this description is to be construed as illustrative only and is for the purpose of teaching those skilled in the art the general manner of carrying out the embodiments. It is to be understood that the forms of the embodiments shown and described herein are to be taken as the presently preferred embodiments. Elements and materials may be substituted for those illustrated and described herein, parts and processes may be reversed, and certain features of the embodiments may be utilized independently, all as would be apparent to one skilled in the art after having the benefit of this description. Changes may be made in the elements described herein without departing from the spirit and scope of the following claims.

What is claimed is:

1. A system, comprising:

a fabric for being worn on a body of a wearer, wherein the fabric comprises one or more layers, at least one layer of fabric comprising a conductive elastic material;

a plurality of respiratory monitoring sensors integrated in the fabric, wherein at least two respiratory monitoring sensors are coupled with at least a portion of the conductive elastic material, and wherein the at least two respiratory monitoring sensors are configured to assess a resistance of the portion of the conductive elastic material between the at least two respiratory monitoring sensors;

one or more inertial measurement units integrated in the fabric, wherein the inertial measurement units are configured to assess a physical position of the body of the wearer in a three-dimensional space;

one or more heart rate monitors integrated in the fabric, wherein the heart rate monitors are configured to assess one or more properties associated with a heart of the wearer; and a processor integrated in the fabric, wherein the processor is configured to receive data from one or more of: the respiratory monitoring sensors, the inertial measurement units, and the heart rate monitors;

wherein the processor is configured to receive GPS data from a GPS monitor integrated in the fabric;

wherein the processor is configured to assess at least some movement of the wearer using the data received from the one or more inertial measurement units and the GPS data from the GPS monitor;

wherein the processor is configured to generate a three-dimensional image of motion and body position of the wearer of the fabric; and wherein the processor is configured to assess one or more vital signs and a body position of the wearer of the fabric using the received data.

2. The system of claim 1, wherein the processor is configured to provide an output indicative of the assessed vital signs and the assessed body position of the wearer of the fabric.

3. The system of claim 1, wherein the processor is coupled to at least one of the respiratory monitoring sensors, the inertial measurement units, or the heart rate monitors with one or more wires distributed through the fabric.

4. The system of claim 1, wherein the processor is wirelessly coupled to at least one of the respiratory monitoring sensors, the inertial measurement units, or the heart rate monitors.

5. The system of claim 1, wherein the layer of the fabric comprising the conductive elastic material is configured to be in contact with the skin of the wearer of the fabric.

6. The system of claim 1, wherein at least two respiratory monitoring sensors are coupled together with a first portion of the conductive elastic material and at least two respiratory monitoring sensors are coupled together with a second portion of the conductive elastic material, the first portion of the conductive elastic material being oriented in a first direction in the fabric and the second portion of the conductive elastic material being oriented in a second direction in the fabric.

7. The system of claim 6, wherein the processor is configured to assess a first resistance of the first portion of the conductive elastic material and assess a second resistance of the second portion of the conductive elastic material.

8. The system of claim 6, wherein the first portion of the conductive elastic material is oriented substantially vertically in the fabric, and wherein the second portion of the conductive elastic material is oriented transversely in the fabric.

9. The system of claim 1, wherein at least one respiratory monitoring sensor comprises a band that encompasses a circumference of the fabric.

10. The system of claim 1, wherein the heart rate monitors comprise leads for electrocardiography sensors.

11. The system of claim 1, wherein at least one of the inertial measurement units is positioned at or near a shoulder portion of the fabric, and wherein at least one of the inertial measurement units is positioned at or near a hip portion of the fabric.

12. The system of claim 1, wherein the inertial measurement units are configured to assess rotation, flexion, and extension of the body of the wearer.

13. A method, comprising:

receiving, in a processor integrated in a fabric, data from a plurality of respiratory monitoring sensors integrated in the fabric, wherein at least two respiratory monitoring sensors are coupled with at least a portion of a conductive elastic material, wherein the data from the respiratory monitoring sensors comprises a resistance of the portion of the conductive elastic material between the at least two respiratory monitoring sensors, wherein the fabric comprises one or more layers, at least one layer of fabric comprising the conductive elastic material;

receiving, in the processor, data from one or more inertial measurement units integrated in the fabric, wherein the data from the inertial measurement units comprises a physical position of the body of the wearer in a three-dimensional space;

receiving, in the processor, GPS data from a GPS monitor integrated in the fabric;

assessing at least some movement of the wearer using the data received from the inertial measurement units and the GPS data received from the GPS monitor; and generating a three-dimensional image of motion and body position of the wearer of the fabric;

receiving, in the processor, data from one or more heart rate monitors integrated in the fabric, wherein the data from the heart rate monitors comprises one or more properties associated with a heart of the wearer; and assessing, using the processor, one or more vital signs and a body position of the wearer of the fabric, wherein the assessing comprises using one or more of: the data received from the respiratory monitoring sensors, the data received from the inertial measurement units, and the data received from the heart rate monitors.

14. The method of claim 13, further comprising providing, from the processor, an output indicative of the assessed vital signs and body position of the wearer of the fabric.

15. The method of claim 13, wherein assessing the body position of the wearer comprises assessing movement of the wearer's body.

16. The method of claim 13, wherein assessing the body position of the wearer comprises assessing the body position of the wearer in a three-dimensional space.

17. The method of claim 13, further comprising assessing a heart rate of the wearer using the data received from the heart rate monitors.

18. The method of claim 13, further comprising assessing a respiration rate of the wearer using data received from the respiratory monitoring sensors.

19. The method of claim 13, further comprising assessing at least some movement of the wearer using the inertial measurement units.

20. The method of claim 13, further comprising tracking a physical location of a body of the wearer using the GPS monitor.

21. The method of claim 20, further comprising tracking physical location of the body of the wearer in near real time on a map overlay.

22. The method of claim 21, wherein the three-dimensional image of motion of the wearer comprises an image of a combination of transverse, sagittal, and frontal motion of the wearer.

* * * * *